(12) United States Patent
Yoshida et al.

(10) Patent No.: US 7,122,698 B2
(45) Date of Patent: Oct. 17, 2006

(54) METHOD FOR PRODUCING α-HYDROXYCARBOXYLATE

(75) Inventors: Hiroshi Yoshida, Suita (JP); Hideaki Tsuneki, Tokyo-to (JP); Toshio Hayashi, Kobe (JP); Hideyuki Baba, Osaka (JP); Takahiro Inagaki, Takatsuki (JP); Satoshi Nakagawa, Suita (JP); Yukihiko Kakimoto, Himeji (JP); Ritsuo Kitada, Takatsuki (JP); Kohei Umehara, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 474 days.

(21) Appl. No.: 10/680,919

(22) Filed: Oct. 8, 2003

(65) Prior Publication Data

US 2005/0090686 A1    Apr. 28, 2005

(30) Foreign Application Priority Data

| Oct. 9, 2002 | (JP) | 2002-296621 |
| Oct. 9, 2002 | (JP) | 2002-296623 |
| Dec. 3, 2002 | (JP) | 2002-350987 |
| Dec. 3, 2002 | (JP) | 2002-350994 |
| Dec. 3, 2002 | (JP) | 2002-350997 |
| Jun. 4, 2003 | (JP) | 2003-158809 |

(51) Int. Cl.
*C07C 69/66* (2006.01)
(52) U.S. Cl. ........................... 560/179
(58) Field of Classification Search ............. None
See application file for complete search history.

(56) References Cited

U.S. PATENT DOCUMENTS

2003/0060655 A1   3/2003 Hayashi, et al.

FOREIGN PATENT DOCUMENTS

| JP | 07-173264 A | 7/1995 |
| JP | 11-292825 A | 10/1999 |

OTHER PUBLICATIONS

Lee et al, Pollimo, Synthesis and Polymerization of New Sequentially ordered Aliphatic Ester Diols, 1997, 21 (6), pp. 926-936, CAS Abstract.*
Biella et al, Catalysis Today, Application of Gold Catalysts to Selective Liquid Phase Oxidation, 2002, 72, pp. 43-49.*

* cited by examiner

*Primary Examiner*—Paul A. Zucker
(74) *Attorney, Agent, or Firm*—Knobbe, Martens, Olson & Bear LLP

(57) ABSTRACT

The present invention provides a process for more efficiently producing an α-hydroxycarboxylic acid ester wherein side reactions due to the α-hydroxycarboxylic acid ester are inhibited or prevented in comparison with prior art production processes.

The invention provides a process for producing an α-hydroxycarboxylic acid ester comprising Steps 1 to 3:

Step 1. reacting, in the presence of oxygen, (i) a 1,2-diol with a 1,2-diol or (ii) a 1,2-diol with an alcohol to obtain a reaction product containing an α-hydroxycarboxylic acid ester;

Step 2. separating the α-hydroxycarboxylic acid ester from the reaction product obtained in Step 1 by distillation under reduced pressure; and Step 3. feeding Step 1 with a mixture obtained by partially or entirely removing water from the reaction product, wherein the mixture contains an unreacted 1,2-diol and/or alcohol.

16 Claims, 3 Drawing Sheets

METHOD FOR PRODUCING α-HYDROXYCARBOXYLATE

TECHNICAL FIELD

The present invention relates to a method for producing an α-hydroxycarboxylic acid ester.

BACKGROUND OF THE INVENTION

Glycolic acid esters, lactic acid esters, and like α-hydroxycarboxylic acid esters have been used as raw materials (condensation polymerization monomers) for various synthetic resins such as polyglycolic acid and the like. Moreover, they are industrially useful compositions as cleaning agents, etchants, etc.

Processes known for producing glycolic acid esters, a type of α-hydroxycarboxylic acid ester, are, for example, those described in the following Items 1 to 4:

1. Synthesizing a polyglycolide from formaldehyde and carbon monoxide in the presence of a heteropolyacid, and then subjecting it to alcoholysis (for example, Japanese Unexamined Patent Publication No. 1994-228045, claims);
2. Producing glycolic acid from formaldehyde and carbon monoxide, and then esterifying it with an alcohol (e.g., Korean Patent Publication No. 9511114);
3. Conducting oxidative esterification between glyoxal and an alcohol in the presence of a catalyst (e.g., Japanese Unexamined Patent Publication No. 1996-104665, claims); and
4. Hydrogenating an oxalic acid diester (e.g., Japanese Unexamined Patent Publication No. 1994-135895, claims).

In view of the processes described above, the present inventors previously developed a production process employing oxidative esterification (see, for example, Japanese Patent Application No. 2002-204748, claims). In this process, an α-hydroxycarboxylic acid ester is produced by reacting a 1,2-diol with an alcohol in the presence of oxygen. This process enables an α-hydroxycarboxylic acid ester to be produced more efficiently.

However, α-hydroxycarboxylic acid esters (especially glycolic acid ester) are unstable to heat and relatively reactive. Therefore, even in the production process disclosed in the aforementioned Patent Application No. 2002-204748 (claims), the desired product may be obtained in reduced yield due to side reactions (such as oligomerization, hydrolysis, ester exchange reactions, etc.) of the α-hydroxycarboxylic acid esters undergoing heating during reaction, distillation and the like. Moreover, since those components having lower boiling points than the α-hydroxycarboxylic acid esters are removed from the system by distillation, it is possible that reaction equilibrium is lost and side reactions are enhanced. Furthermore, the prior art methods are inadequate for integrating the synthesis and purification of α-hydroxycarboxylic acid esters to efficiently produce the desired products. Therefore, demand exists for a more efficient production method for α-hydroxycarboxylic acid esters.

Examples of α-hydroxycarboxylic acid condensates (2-hydroxycarboxylic acid condensates) include polylactic acid, polyglycolic acid, and the like. These compounds are usually obtained by subjecting α-hydroxycarboxylic acids (2-hydroxycarboxylic acids) such as lactic acid, glycolic acid, and the like, to dehydrative condensation (for example, Japanese Unexamined Patent Publication No. 1995-102044, claims). In this case, one terminal of the condensate is a hydroxyl group and the other is a carboxyl group.

Production of α-hydroxycarboxylic acid condensates by dehydrative condensation of α-hydroxycarboxylic acids poses a problem in that it is difficult to produce α-hydroxycarboxylic acid condensates of sufficient molecular weight. Therefore, in practice, such α-hydroxycarboxylic acid condensates are produced by initially preparing condensates having a molecular weight of several thousands to tens of thousands, thermally decomposing them to produce cyclic esters such as lactides and glycolides, and ring-opening polymerizing these cyclic esters.

Also known is a method in which α-hydroxycarboxylic acid condensates are produced by a dealcoholizing condensation reaction using hydroxycarboxylic acid ester such as methyl lactate, butyl lactate, and the like as starting materials. The condensates produced by this method have a hydroxyl group at one terminal and an ester group such as a methyl ester, butyl ester, or like group at the other terminal (for example, Japanese Unexamined Patent Publication 1995-173264, claims). As with the condensates derived from α-hydroxycarboxylic acids, it is difficult to produce such condensates with sufficient molecular weight, and the production process thereof is complex.

Therefore, demand exists for the development of α-hydroxycarboxylic acid condensates that have higher molecular weight than prior art condensates and a process for readily producing them.

DISCLOSURE OF THE INVENTION

As described above, demand exists for a process that can more efficiently produce α-hydroxycarboxylic acid esters, compared with prior art processes, wherein side reactions of the α-hydroxycarboxylic acid esters are inhibited or prevented.

Accordingly, an object of the present invention is to provide a process that can more efficiently produce an α-hydroxycarboxylic acid ester, compared with prior art processes, wherein side reactions of the α-hydroxycarboxylic acid ester are suppressed or prevented.

There is also a demand for α-hydroxycarboxylic acid condensates that have higher molecular weight than prior art α-hydroxycarboxylic acid condensates, and a process for readily producing them.

Therefore, another object of the invention is to provide α-hydroxycarboxylic acid condensates, especially α-hydroxycarboxylic acid condensates having a hydroxyl group at both terminals, of sufficient molecular weight, and a process for readily producing them.

The inventors conducted extensive research in view of the prior art problems and found that a process for producing an α-hydroxycarboxylic acid ester and a process for producing an α-hydroxycarboxylic acid condensate both including specific steps can achieve the objectives described above. The invention has been accomplished based on the above findings.

That is to say, the present invention relates to processes for producing an α-hydroxycarboxylic acid ester and an α-hydroxycarboxylic acid condensate.

1. A process for producing an α-hydroxycarboxylic acid ester comprising Steps 1 to 3:

Step 1. reacting, in the presence of oxygen, (i) a 1,2-diol with a 1,2-diol or (ii) a 1,2-diol with an alcohol to obtain a reaction product containing an α-hydroxycarboxylic acid ester;

Step 2. separating the α-hydroxycarboxylic acid ester from the reaction product obtained in Step 1 by distillation under reduced pressure; and Step 3. feeding Step 1 with a mixture obtained by partially or entirely removing water from the reaction product, wherein the mixture contains an unreacted 1,2-diol and/or alcohol.

2. A process according to Item 1, wherein the distillation of Step 2 is conducted at a pressure of 13 to 80000 Pa and a temperature at the bottom of a distillation column of 30 to 250° C.

3. A process according to Item 1, wherein the mixture in Step 3 contains water in a proportion of 0 to 20 wt. %.

4. A process according to Item 1, wherein when Steps 1 to 3 are in steady state, the reaction ingredients in Step 1 contain water in a proportion of 0.1 to 15 wt. %.

5. A process according to Item 1, wherein in Step 3 at least 30 wt. % of water based on the total weight of water is removed and fed to Step 1.

6. A process according to Item 1, wherein in the distillation of Step 2 the reaction product obtained in Step 1 is formed into a thin film and heated by contacting the thin film with a heating surface.

7. A process according to Item 1, wherein the reaction of Step 1 is conducted in the presence of a catalyst comprising a carrier and fine particles of a noble metal supported on the carrier.

8. A process according to Item 1, wherein the reaction of Step 1 is conducted by further adding an α-hydroxycarboxylic acid and/or α-hydroxycarboxylic acid ester oligomer.

9. A process according to Item 1, wherein a solution obtained at the bottom of a distillation column containing at least one reaction by-product selected from the group consisting of α-hydroxycarboxylic acids and α-hydroxycarboxylic acid ester oligomers generated in Step 1 and/or Step 2 is fed to Step 1 and/or Step 2.

10. A process according to Item 1, wherein a 1,2-diol and an alcohol are reacted in Step 1.

11. A process according to Item 10, wherein the reaction of Step 1 is conducted by further adding at least one member selected from the group consisting of α-hydroxycarboxylic acids, α-hydroxycarboxylic acid 2-hydroxyalkyl esters, and α-hydroxycarboxylic acid ester oligomers.

12. A process according to Item 10, wherein the reaction of Step 1 is conducted in the presence of a catalyst comprising a carrier and fine particles of a noble metal supported on the carrier.

13. A process according to Item 10, wherein in Step 2 a fraction containing the α-hydroxycarboxylic acid ester is collected from a sidecut part.

14. A process according to Item 10, wherein a solution obtained at the bottom of a distillation column containing at least one reaction by-product selected from the group consisting of α-hydroxycarboxylic acids, α-hydroxycarboxylic acid 2-hydroxyalkyl esters and α-hydroxycarboxylic acid ester oligomers generated in Step 1 and/or Step 2 is provided in Step 1 and/or Step 2.

15. A process according to Item 10, wherein a solution obtained at the bottom of a distillation column containing an α-hydroxycarboxylic acid ester oligomer generated in Step 1 and/or Step 2 is contacted with an alcohol R—OH corresponding to the ester group —C(=O)OR of the oligomer, whrein R is an organic residue, and then reused in Step 1 and/or Step 2.

16. A process according to Item 10, wherein the 1,2-diol is ethylene glycol and the α-hydroxycarboxylic acid ester is a glycolic acid ester.

17. An α-hydroxycarboxylic acid condensate selected from (I) to (III) below:

(I) an α-hydroxycarboxylic acid condensate having an α-hydroxycarboxylic acid condensate portion represented by General Formula 2:

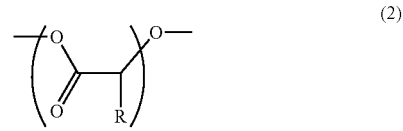

wherein R is hydrogen or $C_{1-5}$ alkyl, and the alkyl may be substituted and a 1,2-diol chain represented by General Formula 3:

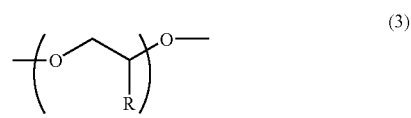

wherein R is hydrogen or $C_{1-5}$ alkyl, and the alkyl may be substituted, both terminals being represented by General Formula 4:

wherein R is hydrogen or $C_{1-5}$ alkyl, and the alkyl may be substituted, or

General Formula 5:

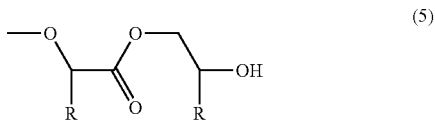

wherein each R is hydrogen or $C_{1-5}$ alkyl, and the alkyl may be substituted;

(II) an α-hydroxycarboxylic acid condensate represented by General Formula 6:

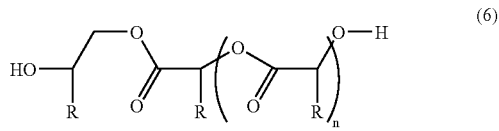

wherein each R is hydrogen or $C_{1-5}$ alkyl, the alkyl may be substituted, and n is within the range of 1 to 200; and (III) an α-hydroxycarboxylic acid condensate represented by General Formula 7:

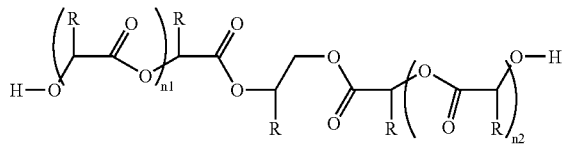

(7)

wherein each R is hydrogen or $C_{1-5}$ alkyl, the alkyl may be substituted, both n1 and n2 are 1 or more, and n1+n2 is within the range of 2 to 200.

18. An α-hydroxycarboxylic acid condensate obtained by condensing, through a 1,2-diol eliminating reaction of an α-hydroxycarboxylic hydroxyalkyl ester prepared according to a process for producing an α-hydroxycarboxylic acid ester comprising reacting, in the presence of a catalyst, 1,2-diols represented by General Formula 1:

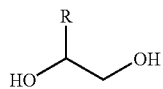

(1)

wherein R is hydrogen or $C_{1-5}$ alkyl, and the alkyl may be substituted, the α-hydroxycarboxylic acid condensate being selected from (I) to (III) below:

(I) an α-hydroxycarboxylic acid condensate having an α-hydroxycarboxylic acid condensate portion represented by General Formula 2:

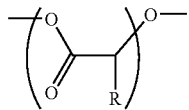

(2)

wherein R is hydrogen or $C_{1-5}$ alkyl, and the alkyl may be substituted and a 1,2-diol chain represented by General Formula 3:

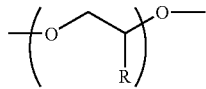

(3)

wherein R is hydrogen or $C_{1-5}$ alkyl, and the alkyl may be substituted, both terminals being represented by General Formula 4:

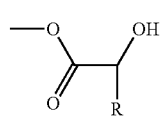

(4)

wherein R is hydrogen or $C_{1-5}$ alkyl, and the alkyl may be substituted, or

General Formula 5:

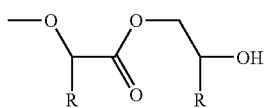

(5)

wherein each R is hydrogen or $C_{1-5}$ alkyl, and the alkyl may be substituted;

(II) an α-hydroxycarboxylic acid condensate represented by General Formula 6:

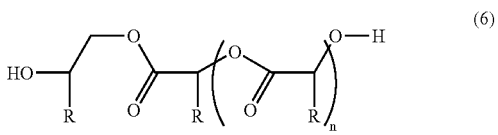

(6)

wherein each R is hydrogen or $C_{1-5}$ alkyl, the alkyl may be substituted, and n is within the range of 1 to 200; and (III) an α-hydroxycarboxylic acid condensate represented by General Formula 7:

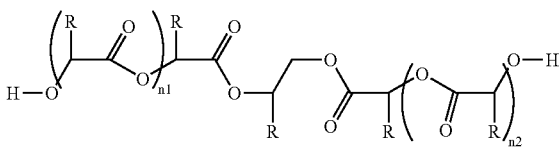

(7)

wherein each R is hydrogen or $C_{1-5}$ alkyl, the alkyl may be substituted, both n1 and n2 are 1 or more, and n1+n2 is within the range of 2 to 200.

19. A process according to Item 1, wherein the distillation of Step 2 is conducted using a multistage distillation column.

20. A process according to Item 19, wherein the distillation of Step 2 is conducted at a pressure of 13 to 80000 Pa and a temperature at the bottom of the distillation column of 30 to 250° C.

21. A process according to Item 19 or 20, wherein a solution obtained at the bottom of the distillation column containing at least one reaction by-product selected from the group consisting of α-hydroxycarboxylic acids and α-hydroxycarboxylic acid ester oligomers generated in Step 2 is sent to Step 1 and/or Step 2.

1. A process for producing an α-hydroxycarboxylic acid ester

A process for producing an α-hydroxycarboxylic acid ester of the present invention comprises Steps 1 to 3 below:

Step 1. reacting, in the presence of oxygen, (i) a 1,2-diol and a 1,2-diol or (ii) a 1,2-diol with an alcohol to obtain a reaction product containing an α-hydroxycarboxylic acid ester;

Step 2. separating the α-hydroxycarboxylic acid ester from the reaction product obtained in Step 1 by distillation under reduced pressure; and Step 3. feeding Step 1 with a mixture obtained by partially or entirely removing water from the reaction product, wherein the mixture contains an unreacted 1,2-diol and/or alcohol.

(Step 1)

In Step 1, (i) a 1,2-diol and a 1,2-diol or (ii) a 1,2-diol and an alcohol are reacted in the presence of oxygen to obtain a reaction product containing an α-hydroxycarboxylic acid ester. As described above, to obtain a reaction product containing an α-hydroxycarboxylic acid ester, either 1,2-diols are reacted together or a 1,2-diol and an alcohol other than 1,2-diols are reacted.

(1) Starting Materials

Examples of 1,2-diols are not limited insofar as they are alcohols having hydroxyl groups at the 1 and 2 positions, e.g., polyols having a valency of 3 or more.

Specifically, examples of 1,2-diols include ethylene glycol, 1,2-propylene glycol, 1,2-butanediol, 1,2-hexanediol, and like aliphatic 1,2-diols having 2 to about 10 carbons; glycerol, erythritol, xylitol, sorbitol, and like aliphatic polyols having hydroxyl groups at the 1 and 2 positions and having about 3 to about 10 carbons; and the like. In addition, derivatives of the aforementioned 1,2-diols can be used.

Examples of such 1,2-diol derivatives include 3-chloro-1,2-propanediol and like halogen-containing aliphatic 1,2-diols having 2 to about 10 carbons; 2-phenyl-1,2-ethanediol and like aliphatic 1,2-diols with an aromatic ring having 2 to about 10 carbons; and the like.

Among these compounds, especially preferable are ethylene glycol and like aliphatic diols having 2 to about 6 carbons. These 1,2-diols and their derivatives can be used alone or in combination.

Examples of alcohols are not limited insofar as not being 1,2-diols. Types of alcohols are not restricted as long as they contain a hydroxyl group within their molecules. Monoalcohols can be used and polyols having a valency of 2 or more can also be used.

Specific examples include methanol, ethanol, 1-propanol, 1-butanol, 1-hexanol, 1-octanol, and like aliphatic alcohols having 1 to about 10 carbons; 1,3-butanediol, 1,4-butanediol, and like aliphatic polyols having about 3 to about 10 carbons; allyl alcohol, methallyl alcohol, and like aliphatic unsaturated alcohols having about 3 to about 10 carbons; benzyl alcohol and like alcohols having an aromatic ring; and the like.

Among these alcohols, primary alcohols, especially $C_{1-4}$ aliphatic primary alcohols, i.e., methanol, ethanol, 1-propanol, and 1-butanol, are preferable. Furthermore, methanol, ethanol, 1-propanol, 1-butanol, and like monoalcohols are most preferable. Such alcohols can be used alone or in combination.

(2) Proportions of Starting Materials

The type of starting materials, i.e., 1,2-diols and alcohols, can be suitably selected depending on the type of the desired α-hydroxycarboxylic acid ester.

For example, when a glycolic acid ester is to be produced, ethylene glycol is selected as the 1,2-diol and a primary alcohol such as methanol, ethanol, 1-propanol, 1-butanol, or the like is selected as the alcohol. In case of using a 1,2-diol alone, for example, when ethylene glycol alone is used as the 1,2-diol, a glycolic acid 2-hydroxyethyl ester is produced.

When a 1,2-diol and an alcohol are used as starting materials, the proportion of these ingredients is not limited. The molar ratio of 1,2-diol to alcohol is usually 1:2 to 1:50, and preferably 1:3 to 1:20. Molar ratios adjusted to within this range can efficiently produce α-hydroxycarboxylic acid esters.

(3) Catalysts

When (i) a 1,2-diol and a 1,2-diol or (ii) a 1,2-diol and an alcohol are reacted in the presence of oxygen, the reaction may be conducted in the presence of a catalyst as necessary.

(a) Catalytically Active Ingredients

Types of catalysts are not limited. Preferable catalysts are those in which metals, i.e., active ingredients, are supported by carriers, i.e., supported metal catalysts.

Although metals, i.e., active ingredients, are not limited, noble metals are preferable. Examples include gold, palladium, ruthenium, rhodium, iridium, platinum, and the like. Among these, gold, palladium and ruthenium are more preferable, with gold being most preferable.

It is preferable that catalysts contain noble metal(s) described above, and it is preferable that catalysts further contain, besides noble metal(s), at least one element selected from Groups 2B, 3B, 4B, 5B and 6B of Periods 4 to 6, and Group 8 of Period 4 of the periodic table published by Maruzen, Japan (Chemical Analysis Manual, $5^{th}$ edition, 2001) (hereinafter these elements are sometimes referred to as "secondary elements"). Examples of secondary elements include Zn, Cd, Hg, and the like of Group 2B; Ga, In, Tl, and the like of Group 3B; Ge, Sn, Pb, and the like of Group 4B; As, Sb, Bi, and the like of Group 5B; Se, Te, Po, and the like of Group 6B; Fe, Co, Ni, and the like of Group 8; etc.

Specifically, when a catalyst is used, preferably used is that in which particles, for example, composed of Au fine particle and/or fine particles composed of at least one secondary element selected from Periods 4 to 6 and Groups 2B, 3B, 5B, 6B, and Period 4 and Group 8 of the periodic table and Au are supported by a carrier.

When metals, i.e., active ingredients, include noble metals as described above, the noble metals can be used alone or in combination. When two or more noble metals are used, insofar as the effects of the invention are not impaired, they may partly or entirely form an alloy, intermetallic compound, or the like.

Moreover, when metals, i.e., active ingredients, include noble metals and secondary elements, insofar as the effects of the invention are not impaired, the noble metals and the secondary elements can partly or entirely form an alloy, intermetallic compound, or the like. Noble metals and secondary elements are usually supported by carriers. Catalysts usable in the process of the invention, insofar as the effects of the invention are not impaired, can contain impurities and other elements besides the noble metals and secondary elements.

The particle diameter of the active ingredients, i.e., metal particles, is not limited inasmuch as the desired catalytic activities can be obtained. The average particle diameter is usually no more than about 10 nm, preferably no more than about 6 nm, more preferably no more than about 5 nm, and especially preferably about 1 to about 5 nm. An average particle diameter within this range more consistently provides particles with excellent catalytic activities. Although the lowest value for the average particle diameter is not limited, in view of physical stability, about 1 nm is preferable.

In the present invention, the average particle diameter of the metal particles refers to an arithmetic mean value calculated as follows: 120 metal particles are randomly selected while observing through a transmission electron microscope; the 10 particles having the 10 largest diameters and the 10 particles having the 10 smallest diameters are eliminated, totaling 20 particles; and the arithmetic mean value of the particle diameter of remaining 100 particles is calculated. The peak in the particle diameter distribution of the metal particles is preferably found within the range of about 1 to about 6 nm, and especially within the range of about 1 to about 5 nm. A narrow particle diameter distribution is preferable, and the standard deviation for the diameter of the 120 particles is preferably no more than about 2 nm, and especially no more than about 1.5 nm.

The amount of metal active-ingredients supported in the catalyst can be suitably selected according to the type and similar of carrier. Usually, it is preferably about 0.01 to about 20 parts by weight, and especially about 0.1 to about 10 parts by weight based on 100 parts by weight of carrier.

(b) Carriers

Carriers are not limited herein since compounds that have been used as catalyst carriers can be used as carriers. Commercial products can be used, for example. Those produced according to known methods can also be used. Examples include inorganic oxides, such as metal oxides (silica, alumina, titania, zirconia, magnesia, etc.), complex metal oxides (silica-alumina, titania-silica, silica-magnesia, etc.), zeolites (ZSM-5 and the like), mesoporous silicates (MCM-41 and the like), etc.; natural minerals (clay, diatomaceous earth, pumice, etc.); carbon materials (activated carbon, graphite, etc.); and various other like carriers. Among these examples, inorganic oxides are preferable.

Inorganic oxide carriers are preferably porous. The specific surface area (BET method) thereof is preferably no less than about 50 $m^2/g$, preferably no less than about 100 $m^2/g$, and especially preferably about 100 to about 800 $m^2/g$. The shape and size of carriers are not limited, and can be determined according to the application of final products.

(c) Production Method for Catalysts

Production methods for catalysts are not limited insofar as carriers like those described above can be obtained. For example, a catalyst can be produced by heat-treating a carrier containing at least a desired metal or compound thereof. Examples of metal compounds include hydroxides, chlorides, carboxylate, nitrates, alkoxides, acetylacetonates, etc.

Specifically, when gold fine particles are supported for example, methods are not limited insofar as gold fine particles can be affixed to a carrier. Examples of supporting methods include coprecipitation, deposition precipitation, impregnation, vapor deposition, and like known methods. Among these methods, coprecipitation and deposition precipitation are preferable, with deposition precipitation being especially preferable. When deposition precipitation is employed to produce a catalyst usable in Step 1, a catalyst can be produced, for example, by mixing a solution of a water-soluble compound containing gold with an inorganic oxide carrier, and calcining the solids thus precipitated.

Moreover, when two or more metals are supported on a carrier, the order of supporting the metals is not limited. Any metal can be supported first, and the metals may be supported simultaneously as well. In particular, methods may be classified as (A) noble metals are supported on a carrier first, and then secondary elements are supported; (B) secondary elements are supported on a carrier first, and noble metals are then supported; and (C) noble metals and secondary elements are supported simultaneously on a carrier.

(4) Reaction Conditions

The reaction between (i) a 1,2-diol and a 1,2-diol or (ii) a 1,2-diol and an alcohol in the presence of oxygen can be a liquid-phase, vapor-phase, or like reaction. Molecular oxygen is preferable as the oxygen. Oxygen (oxygen gas) can be diluted with nitrogen, argon, helium, carbon dioxide, or like inert gases. Moreover, atmospheric air or like oxygen-containing gases can be used. Methods for supplying an oxygen-containing gas to the reaction system are not limited, and known methods can be employed. Especially, bubbling through a solution is suitably employed.

The mode of the aforementioned reaction is not restricted, and a continuous, batch, semibatch or like process can be employed. When a batch process is employed to carry out the reaction, a catalyst is introduced simultaneously with the starting materials into a reactor. When a continuous process is employed to carry out the reaction, a catalyst is either charged into the reactor beforehand or continuously introduced thereto together with the starting materials. The catalyst is used in a fixed, fluidized, suspended or like bed.

Specific examples of reaction equipment are given hereinafter: (i) an external circulation reactor wherein a catalyst is immobilized in the reactor, starting materials in which an oxygen-containing gas is dissolved are continuously supplied thereto, the removed reaction solution is remixed with an oxygen-containing gas, and the reaction solution is directed back to the reactor; (ii) a tubular reactor wherein a catalyst is immobilized in the tubular reactor, and starting materials and an oxygen-containing gas are continuously supplied thereto; (iii) a perfusate-packed column reactor wherein a catalyst is charged into a column reactor, and starting materials and an oxygen-containing gas are continuously supplied thereto; and similar reactors. Among these reactors, when reactor (ii) is used, the oxygen-containing gas is dividedly supplied from a plurality of locations (such as inlet port, middle sections and the like of the reactor) to enhance reaction efficiency. When reactor (iii) is used, reaction efficiency can be increased by creating a continuous phase of the gas and a disperse phase of the reaction solution.

When a catalyst is used in a suspended or fluidized bed, for example, (iv) a tank reactor can be used wherein starting materials and a catalyst are introduced into a tank reactor, and the reaction is carried out while an oxygen-containing gas is continuously supplied thereto. In this case, a batch process may be employed in which starting materials and a catalyst are introduced simultaneously at the beginning, as well as a semibatch process in which portions of starting materials are supplied continuously or batch-wise during reaction. Moreover, a continuous process can also be employed in which starting materials and an oxygen-containing gas are continuously supplied, and the reaction solution and the gas are continuously removed. When the reaction is carried out continuously, reaction efficiency can be enhanced by the use of continuous tank reactors wherein the reaction is conducted in a plurality of reactors connected in series. (v) A column reactor having interior partitions may also be used. Column reactors include, for example, a vertical continuous tank reactor in which starting materials and a catalyst are continuously supplied from the top of the column and an oxygen-containing gas is introduced from the bottom to conduct the reaction by contacting them as countercurrents. When a continuous tank reactor is used, the reaction solution may be disposed of or may be sent back to the reactor. (vi) A bubble column reactor can also be used in which starting materials and an oxygen-containing gas are continuously introduced from the bottom of the column reactor.

The reaction time is not limited and varies according to the reaction conditions selected. The reaction time is usually about 0.5 to about 30 hours and preferably about 1 to about 20 hours, calculated as a residence time (amount of solution residing in a reactor/amount of solution supplied).

Miscellaneous conditions such as reaction temperature, reaction pressure and the like are suitably selected according to the type of 1,2-diols, alcohols, and catalysts. The reaction temperature is usually about 0 to about 200° C., and preferably about 50 to about 180° C. By adjusting the temperature to within this range, reaction progresses more efficiently. Although the reaction can be carried out under reduced, atmospheric, or increased pressures, the preferable reaction pressure is usually about 0.05 to about 10 MPa (gauge pressure), and especially about 0.1 to about 5 MPa. To inhibit by-product generation, the pH of the reaction system is preferably about 2 to about 9. To control pH, for example, alkali metal compounds and alkaline-earth metal compounds (carboxylates) can be used as additives to the reaction system.

The aforementioned reaction can be conducted in the presence of a solvent. Through the use of a solvent, the desired α-hydroxycarboxylic acid ester is likely to be obtained efficiently. Types of solvents usable herein are not limited insofar as they can dissolve the starting materials, i.e., 1,2-diols and alcohols, and do not react under the aforementioned reaction conditions. Therefore, solvents can be suitably selected according to the types of the starting material alcohols and reaction conditions. Examples, in addition to water, include diethyl ether, diisopropyl ether, dioxane, and like ethers; toluene, xylene, benzene, and like aromatic hydrocarbons; methylene chloride, chloroform, ethylene dichloride, and like halogenated compounds; and the like. The amount of solvent to be used is suitably selected according to the type of solvents, alcohols, catalysts, etc. Through such a reaction as described above, a reaction product containing an α-hydroxycarboxylic acid ester is obtained.

The reaction of Step 1 can be carried out also in the presence of an α-hydroxycarboxylic acid and/or α-hydroxycarboxylic acid ester oligomer (specific substrates). Hereinafter, unless specified otherwise, with respect to the reaction between 1,2-diols and alcohols, α-hydroxycarboxylic acid 2-hydroxyalkyl esters (specific substrate) are included as compounds that can be added to the reaction.

The desired product, α-hydroxycarboxylic acid ester, can be produced more efficiently by conducting the reaction in the presence of a specific substrate. Reasons are:

α-hydroxycarboxylic acid esters have within their molecules hydroxyl group(s) and ester group(s), thereby being highly reactive compounds. Therefore, once produced in a reactor, they easily undergo side reactions. For example, α-hydroxycarboxylic acid esters sometimes undergo an ester exchange reaction and form α-hydroxycarboxylic acid ester oligomers. Also, when a 1,2-diol and an alcohol are reacted, an α-hydroxycarboxylic acid ester and the starting material, i.e., 1,2-diol, sometimes undergo an ester exchange reaction resulting in the production of an α-hydroxycarboxylic acid 2-hydroxyalkyl ester. Furthermore, due to the generation of water in the reaction, the α-hydroxycarboxylic acid ester can be hydrolyzed by the water, generating an α-hydroxycarboxylic acid. These side reactions reduce the amount of the desired α-hydroxycarboxylic acid ester produced. Furthermore, the α-hydroxycarboxylic acid generated by hydrolysis in the presence of water functions as an acid catalyst and promotes the aforementioned side reactions. However, the side reactions described above are equilibrium reactions. Therefore, these side reactions can be suppressed by introducing to the reactor an α-hydroxycarboxylic acid and/or α-hydroxycarboxylic acid ester oligomer as by-products (an α-hydroxycarboxylic acid 2-hydroxyalkyl ester may be added when a 1,2-diol and an alcohol are reacted. Same applies hereinbelow.), thereby reducing the apparent rate of the side reactions.

α-hydroxycarboxylic acid ester oligomers are condensation polymers in which α-hydroxycarboxylic acid esters and/or α-hydroxycarboxylic acids are connected by an ester bond. Examples thereof include α-hydroxycarboxylic acid ester oligomers wherein a terminal of each oligomer is an alcohol ester, α-hydroxycarboxylic acid 2-hydroxyethyl oligomers wherein a terminal of the oligomer is an ethylene glycol ester, and α-hydroxycarboxylic acid oligomers wherein a terminal of the oligomer is a carboxylic acid formed by hydrolysis.

The oligomers have at least 2 repeating units that are represented by —O—$CH_2$—C— (=O)—. The maximum number of repeating units is not limited. However, the excessively large number of repeating units may reduce reactivity and impairs handling properties by increasing melting point and viscosity. Therefore, the number of repeating units is preferably 100 at most.

The amount of α-hydroxycarboxylic acid and/or α-hydroxycarboxylic acid ester oligomer to be added is preferably 0.1 mol % or more, and more preferably 0.3 mol % or more, based on the 1,2-diol of the starting materials.

An α-hydroxycarboxylic acid and/or α-hydroxycarboxylic acid ester oligomer can be mixed with the reaction ingredients prior to reaction, and can also be added during reaction. Although details will be provided hereinafter, the addition of these specific substrates as mentioned above can be substituted by reusing in Step 1 the solution obtained at the bottom of a distillation column that contains the reaction by-products generated in Step 1 and/or Step 2.

(Step 2)

In Step 2, the reaction product obtained in Step 1 is distilled under reduced pressure to isolate the α-hydroxycarboxylic acid ester. The pressure is not limited but usually refers to a pressure of about 1 to about 100000 Pa as preferable, more preferably about 13 to about 80000 Pa. Distillation conducted under reduced pressure keeps the temperature inside the distillation column low, thereby inhibiting side reactions.

The reaction product obtained in Step 1 contains, other than the desired α-hydroxycarboxylic acid ester, unreacted 1,2-diol and alcohol, generated water, etc. By distilling the reaction product under reduced pressure, the α-hydroxycarboxylic acid ester can be separated.

This reaction product can be subjected to distillation under reduced pressure, or it can be distilled after being subjected to other treatments. Other treatments refer to, for example, separation treatment to separate solids such as catalysts and the like, evaporation treatment to remove low-boiling-point components, reaction treatment to convert by-products in the reaction solution into useful components, pre-distillation treatment to condition the composition of the reaction solution for stable distillation, etc.

Distillation methods include simple distillation and rectification using a multistage distillation column. Rectification is preferable. Preferable modes of distillation include batch distillation and continuous distillation.

When a multistage distillation column is used, although the number of stages is not limited, a distillation column having 2 or more stages is preferable, provided that the column top (the highest stage) and the column bottom (the lowest stage) are not counted as stages. Examples of usable columns are those generally used such as packed columns in which packings, e.g., Raschig rings, Pall rings, Intalox saddles, Dickson packings, McMahon packings, Sulzer packings, etc., are furnished inside; trayed columns having trays such as bubble cap trays, sieve trays, valve trays, and the like. Moreover, complex distillation columns can be used that are equipped with trays and packing layers. A plurality of multistage distillation columns can be used in combination. The number of stages refers to the number of trays in trayed columns and refers to the number of theoretical stages in packed columns.

Distillation methods to isolate the α-hydroxycarboxylic acid ester from the reaction product are not limited. The most suitable method can be selected according to the composition of the reaction product. A plurality of distillation columns can be used. In such a case, either low-boiling-point components may be separated first, or high-boiling-point components may be separated first.

When the reaction product contains components having a boiling point higher than that of the α-hydroxycarboxylic acid ester and components having a boiling point lower than that of the α-hydroxycarboxylic acid ester, the α-hydroxycarboxylic acid ester is separated by continuous distillation, it is preferably withdrawn from a sidecut part provided in the middle of the distillation column. α-hydroxycarboxylic acid esters undergo side reactions with heating. Therefore, withdrawing the α-hydroxycarboxylic acid ester from the middle of the distillation column without it dropping to the bottom where temperature is higher can allow distillation to proceed without causing side reactions. To inhibit side reactions, it is preferable to withdraw from a sidecut part at least 50% of the α-hydroxycarboxylic acid ester contained in the reaction product supplied to a distillation column.

When a sidecut type column is employed, the configuration of the distillation column is not limited insofar as it has a sidecut part. Therefore, a generally used configuration equipped with a reboiler, condenser, etc., can be used. It is preferable to create a sidecut part where a relatively high concentration of α-hydroxycarboxylic acid ester accumulates in the distillation column. The location of a sidecut part is elsewhere other than the column top or bottom, and can be suitably selected according to the composition of the mixture, distillation conditions (location of the stage to which the reaction product is supplied), etc. For example, when an α-hydroxycarboxylic acid ester obtained from a sidecut part is to have little low-boiling-point components contained therein, it is preferable to withdraw the α-hydroxycarboxylic acid ester from a sidecut part provided below the stage from which the reaction product is supplied. When high-boiling-point components are to be reduced, it is preferable to withdraw the α-hydroxycarboxylic acid ester from a sidecut part provided above the stage from which the reaction product is supplied. To obtain an α-hydroxycarboxylic acid ester with higher purity from a sidecut part, coupling type distillation column such as Petlyuk type distillation column may be used. By employing such a configuration, (1) a fraction containing concentrated low-boiling-point components can be withdrawn from the column top, (2) a fraction containing an α-hydroxycarboxylic acid ester can be removed from a sidecut part, and (3) a solution containing a high concentration of high-boiling-point components can be obtained from the bottom of a column.

As described hereinbelow, when unreacted starting materials are reused in the other step after removing water from the reaction product, water may be removed in Step 2. Water, together with low-boiling-point alcohols, can be withdrawn from the top of a distillation column, and water and alcohol are isolated by a separate distillation. Alternatively, using a single distillation column provided with 2 sidecut lines, alcohol may be withdrawn from the top of the distillation column, water may be removed via the first sidecut part, the α-hydroxycarboxylic acid ester may be removed via the second sidecut part, and the 1,2-diol may be removed from the bottom of the distillation column.

Moreover, if large amounts of low-boiling-point components are contained in the reaction product, distillation can be conducted after lowering the amounts of low-boiling-point components by flash distillation, evaporation, etc.

To inhibit side reactions in a distillation column, it is preferable to minimize the thermal history of the reaction solution in the distillation column as much as possible. As a means to heat the solution, a thin film reboiler and like devices that can minimize thermal history are preferable. Specifically, the reaction product is preferably heated after forming it into a thin film and contacting the film with a heating surface. Such heating is preferably conducted, for example, using a thin film evaporator that can reduce thermal history. Film evaporators are not limited and examples thereof include rising film evaporators, falling film evaporators, rotary film evaporators and like known evaporators. Heating conditions are as known. Therefore, by supplying a solution containing the reaction product to a film evaporator, the solution containing the reaction product is contacted with a heating surface in the manner of a film and heated, thereby shortening the time spent heating the reaction product and effectively inhibiting side reactions undergone by the α-hydroxycarboxylic acid ester.

In the present invention, the pressure in a distillation column upon distilling an α-hydroxycarboxylic acid ester and the temperature at the bottom of the column are important in obtaining products with high purity and yield and minimum color. To inhibit side reactions in a distillation column, distillation is conducted at a pressure of 13 to 80000 Pa or at a column bottom temperature of 30 to 250° C.

The reflux ratio at the top of the distillation column is not limitative. Preferable is 0.1 to 100, with 0.3 to 50 being more preferable. Other operating conditions are in conformity with known distillation conditions.

Through such a distillation procedure as described above, an α-hydroxycarboxylic acid ester can be separated from the reaction product obtained in Step 1.

As described above, α-hydroxycarboxylic acid esters have within their molecules hydroxyl group(s) and ester group(s), thereby being highly reactive. Therefore, by being heated during reacting or distillation, they easily undergo side reactions. For example, α-hydroxycarboxylic acid ester molecules sometimes undergo an ester exchange reaction and form oligomers wherein a plurality of α-hydroxycarboxylic acid ester molecules are connected by ester bond. When there is a coexisting alcohol other than the alcohol R—OH corresponding to the ester group —C=(O)OR (provided R is an organic residue) of the α-hydroxycarboxylic acid ester, this alcohol and the α-hydroxycarboxylic acid ester sometimes undergo an ester exchange reaction and form another α-hydroxycarboxylic acid ester having a different ester group. Moreover, when water coexists, an α-hydroxycarboxylic acid is generated by the hydrolysis of the α-hydroxycarboxylic acid ester. Due to these side reactions, the amount of the desired α-hydroxycarboxylic acid ester is reduced. Furthermore, because the α-hydroxycarboxylic acid generated by hydrolysis in the presence of water is a carboxylic acid, it functions as an acid catalyst and further promotes side reactions. Especially in the reaction step of the invention (Step 1), 2 moles of water is generated per mole of α-hydroxycarboxylic acid ester. Therefore, during the distillation of the reaction solution, hydrolysis and the other aforementioned side reactions are highly likely to occur.

The aforementioned side reactions generate the alcohol R—OH corresponding to the ester group —C(=O)OR (provided R is an organic residue) of the α-hydroxycarboxylic acid ester. Therefore, if this alcohol has a lower boiling point than that of the α-hydroxycarboxylic acid ester and is distilled off first in the distillation process, the equilibrium of the side reactions is shifted as a result, further promoting side reactions.

To prevent or inhibit such side reactions (during reaction or distillation), it is preferable, for example, to reuse in Step 1 and/or Step 2 the solution obtained at the bottom of the distillation column containing at least one reaction by-product selected from the group consisting of α-hydroxycarboxylic acids and α-hydroxycarboxylic acid ester oligomers generated in Step 2. The reasons that side reactions are suppressed or prevented are as described above in relation to Step 1. The solution obtained at the bottom of a distillation column refers to the solution obtained at the bottom of a distillation column after the α-hydroxycarboxylic acid ester is removed therefrom (distilled off) by distillation. This column bottom solution can be fed per se; or this solution can be further distilled to obtain a fraction containing components having a boiling point higher than that of the α-hydroxycarboxylic acid ester, and this fraction can be reused or the column bottom solution obtained from this further distillation can be used.

The solution obtained at the bottom of the distillation column after removing the α-hydroxycarboxylic acid ester through such distillation as described above contains the α-hydroxycarboxylic acid, α-hydroxycarboxylic acid ester oligomer, etc., that are the by-products generated in the reaction and distillation steps to obtain the α-hydroxycarboxylic acid ester. The column bottom solution may further contain other components such as the α-hydroxycarboxylic acid esters or unreacted starting materials.

The column bottom solution is supplied in Step 1 and/or Step 2. As described above, the side reactions that occur in Step 1 and Step 2 are equilibrium reactions. Therefore, by introducing the column bottom solution containing the reaction by-products, the reaction step and/or distillation step are conducted from the beginning in the presence of compounds as by-products thereof, thereby reducing the apparent reaction rate of additional by-products generation. As a result, the yield of α-hydroxycarboxylic acid ester in the reaction step is increased, and the efficiency of α-hydroxycarboxylic acid ester purification by the distillation step is enhanced. Depending on the amount of column bottom solution reused, the starting material alcohol may react with at least one reaction by-product selected from an α-hydroxycarboxylic acid, α-hydroxycarboxylic acid 2-hydroxyalkyl ester, and α-hydroxycarboxylic acid ester oligomer contained in the column bottom solution, and form the desired α-hydroxycarboxylic acid ester, thereby further contributing to improved yield in the reaction step and improved purification efficiency in the distillation step. Moreover, the reuse of reaction by-products as useful components has the effect of reducing the amount of materials to be disposed.

Moreover, instead of providing the column bottom solution in Step 1 and/or Step 2 as it is, it can be fed after contacting with the starting material alcohol. The starting material alcohol refers to the alcohol R—OH that corresponds to the ester group —C(=O)OR (provided that R is an organic residue) of the α-hydroxycarboxylic acid ester. In this case, an α-hydroxycarboxylic acid ester is produced by the esterification between the α-hydroxycarboxylic acid and the alcohol, ester exchange reaction between α-hydroxycarboxylic acid 2-hydroxyalkyl ester and the alcohol, or alcoholysis of the α-hydroxycarboxylic acid ester oligomer.

These above reaction are equilibrium reactions. Therefore, the use of an excess of alcohol results in a high yield of α-hydroxycarboxylic acid ester. Although the amount of alcohol to be used depends on the composition of the column bottom solution, it is preferably equal to or greater than the amount by weight of the column bottom solution, and more preferably twice or greater. The preferable reaction temperature is 30 to 200° C., and more preferably 40 to 180° C. When the temperature is 30° C. or lower, the reaction proceeds slowly, being inefficient. When the temperature exceeds 200° C., side reactions may occur.

The reaction carried out by contacting the column bottom solution with the starting material alcohol can be carried out in the presence of a catalyst. Examples of catalysts include acids; bases; titanium, lead, tin, and like metal compounds; etc. Acids are preferable among these catalysts. Examples of acid catalysts include hydrochloric acid, nitric acid, sulfuric acid, phosphoric acid, heteropolyacids, p-toluenesulfonic acid, acetic acid, and like homogeneous catalysts; and acidic ion-exchange resins, zeolites, clay, and like heterogeneous catalysts. Among these catalysts, heterogeneous catalysts are preferable for ease of separation.

The column bottom solution after reaction with the alcohol may be fed in the reaction step (Step 1), or may be sent to the distillation step (Step 2) to recover through distillation the α-hydroxycarboxylic acid esters (glycolic acid ester) produced from the reaction with the alcohol.

Among α-hydroxycarboxylic acid esters, glycolic acid ester can be produced by the reduction of oxalic acid diesters, by oxidative esterification of ethylene glycol as in the present invention, or by a similar manner. However, by the reduction of oxalic acid diesters, reaction products are obtained wherein unreacted oxalic acid diesters and the desired glycolic acid ester are mixed. By the oxidative esterification of ethylene glycol, when both terminals of ethylene glycol are oxidatively esterified, oxalic acid diesters are generated as by-products. A glycolic acid ester and an oxalic acid diester have similar boiling points, and their vapor-liquid equilibrium curves are asymptotic to the Y=X line. Therefore, they are difficult to isolate by distillation and it is difficult to obtain a glycolic acid ester of high purity with little oxalic acid diester content.

The inventors conducted research on separating a glycolic acid ester from an oxalic acid diester by distillation, and found the following:

First of all, the inventors found that an oxalic acid diester and water form an azeotrope. When a mixture of a glycolic acid ester and an oxalic acid diester is distilled in the presence of water, the oxalic acid diester forms an azeotrope with water and is distributed above the glycolic acid ester in a distillation column. Therefore, the oxalic acid diester can be readily separated. As a result, a glycolic acid ester having a smaller oxalic acid diester content can be obtained than when it is distillated in the absence of water.

Moreover, the inventors found that an oxalic acid diester is more easily hydrolyzed than a glycolic acid ester. When distilled in the presence of water, an oxalic acid diester is hydrolyzed in a distillation column and forms the oxalic acid monoester and oxalic acid, which have high boiling points due to their carboxyl groups. Their respective boiling point differences from the glycolic acid ester is large. Therefore, a glycolic acid ester having a small oxalic acid diester content can be obtained by distillation.

An oxalic acid diester, when compared with a glycolic acid ester, is more likely to undergo an ester exchange reaction with an alcohol (hereinafter referred to as "other alcohol") that is different from the alcohol constituting the ester group. When distilled in the presence of the other alcohol, the oxalic acid diester forms an ester with the other alcohol. When the other alcohol has a boiling point lower than the alcohol constituting the ester group, the oxalic acid diester produced by ester exchange exhibits a boiling point lower than the glycolic acid ester, thereby being easy to separate. Moreover, when the other alcohol has a boiling point higher than the alcohol constituting the ester group, the oxalic acid diester produced by ester exchange exhibits a boiling point higher than the glycolic acid ester, thereby also being easy to separate.

Furthermore, the inventors found that, by distilling a mixture of a glycolic acid ester and an oxalic acid diester in the presence of water and/or the other alcohol as described above, a high-purity glycolic acid ester having a small oxalic acid diester content can be obtained.

To describe this process in detail, for example, when methyl glycolic acid ester is produced by an oxidative esterification between methanol and ethylene glycol, dimethyl oxalate is generated as a by-product wherein both terminals of the ethylene glycol are oxidatively esterified. It is difficult to isolate methyl glycolic acid ester and dimethyl oxalate by distillation because they have similar boiling points and their vapor-liquid equilibrium curves are asymptotic to the Y=X line. However, the reaction solution of this oxidative esterification contains water as a by-product and ethylene glycol, which is an alcohol different from the methanol that constitutes dimethyl oxalate and the like. Therefore, when this reaction solution is distilled, a portion of the dimethyl oxalate forms an azeotrope with water and is separated as a fraction lighter than the glycolic acid ester. Moreover, a portion of the dimethyl oxalate is hydrolyzed in a distillation column and forms monomethyl oxalate, oxalic acid, and the like, and is removed from the bottom of the column as components heavier than the glycolic acid ester. Furthermore, a portion of the dimethyl oxalate undergoes an ester exchange reaction with ethylene glycol in the distillation column and forms heavy components such as 2-hydroxyethyl methyl oxalate, bis(2-hydroxyethyl)oxalate, and the like. These heavy components have a boiling point higher than that of the methyl glycolate and are taken out from the bottom of the column.

As described above, the oxidative esterification employed in the present invention can readily produce through distillation a high-purity glycolic acid ester compared with other methods.

(Step 3)

In Step 3, water is partially or entirely removed from the reaction product obtained in Step 1, and a fraction containing an unreacted 1,2-diol and/or alcohol is reused in Step 1.

In the production of the α-hydroxycarboxylic acid ester, when conversion of the starting materials does not reach 100%, unreacted materials are present in the reaction product obtained in Step 1. Therefore, by partially or entirely removing water from the reaction product obtained and reusing a fraction containing the unreacted 1,2-diol and/or alcohol, an α-hydroxycarboxylic acid ester can be efficiently produced. Methods for partially or entirely removing water are not limited. Water can be removed by distillation, extraction, or like known methods.

Step 3 can be applied to the reaction product obtained in Step 1 (the reaction product that has not undergone Step 2) or the reaction product after Step 2 (the reaction product from which an α-hydroxycarboxylic acid ester has been removed through Step 2). Furthermore, Step 3 can be conducted simultaneously with Step 2.

In partially or entirely removing water from the reaction product, it is preferable to partially or entirely remove water such that the fraction to be sent to Step 1 contains water in a proportion of 0 to 20 wt. %. The water content of the fraction to be reused in Step 1 refers to, when the unreacted 1,2-diol is supplied back, the water content of the fraction containing the unreacted 1,2-diol but not the alcohol. When the unreacted alcohol is supplied back, it refers to the water content of the fraction containing the unreacted alcohol but not 1,2-diol. When both unreacted 1,2-diol and alcohol are reused, it refers to the water content of the entire fraction. If a fraction having a water content of more than 20 wt. % is reused in Step 1, the α-hydroxycarboxylic acid ester produced during the reaction can be hydrolyzed, resulting in a reduced yield of the α-hydroxycarboxylic acid ester. Moreover, the α-hydroxycarboxylic acid generated from hydrolysis can be further oxidized, and water and carbon dioxide may be produced.

Although the amount of water removed from the reaction product varies according to the water content of the mixture to be reused in Step 1, it is usually preferable to remove 30 wt. % or more of water contained in the reaction product.

When the unreacted starting materials are supplied back to the reaction step (Step 1), the amount of newly supplied starting materials to conduct further reaction corresponds to the amount used in the previous reaction and lost in the purification. It is preferable to control the conditions of water removal in Step 3 such that the reaction ingredients used in Step 1 contain water in a proportion of 0.1 to 15 wt. % when Steps 1 to 3 come to steady state by the reuse of the unreacted starting materials. Steady state refers to, when both reaction and distillation are conducted continuously, a state in which the concentration of compounds present in reaction and distillation is constant, and when both reaction and distillation are conducted batch-wise, steady state refers to a state subsequent to the $4^{th}$ cycle if one cycle consists of Steps 1 to 3.

The mode for carrying out the present invention is described below with reference to the drawings. The production of an α-hydroxycarboxylic acid ester by reacting a 1,2-diol with an alcohol is described with reference to FIG. 1 using, for example, two continuous stirred tank reactors as reactors and a distillation column having two sidecut lines.

As shown in FIG. 1, the reaction setup consists of continuous stirred tank reactors 11 and 12 and distillation column 13. Both reactors 11 and 12 are equipped with a stirrer and heater. Feed pipe 21 is connected to Reactor 11, and pipe 24 is connected to the upper part of reactor 11. Pipe 24 functions as a ingredient feed pipe to reactor 12. Pipe 25 is connected to the upper part of reactor 12, thereby allowing reaction products to be supplied to distillation column 13. In the middle of the distillation column, sidecut pipes 28 and 29 are provided to withdraw liquid from a sidecut part. The top of distillation column 13 and feed pipe 21 are connected via pipe 26, and thereby some fractions from distillation column 13 can flow back to reactor 11.

The reaction ingredients, 1,2-diol and alcohol, are continuously fed into reactor 11 through ingredients feed pipe 21. Catalysts can be supplied to the reactor beforehand, or can be supplied with the reaction ingredients. The reaction solution is heated while stirring. Reaction is carried out at a specific temperature under a specific pressure while supplying air (oxygen-containing gas) to the reaction solution to produce an α-hydroxycarboxylic acid ester.

The portion of the reaction solution exceeding a predetermined fluid level is introduced into reactor 12 via pipe 24 and the reaction is continued therein. When a catalyst is used in a suspended bed, the catalyst is subsequently separated from the reaction solution, wherein the catalyst is suspended, by a liquid/solid separator (not shown), and only the reaction solution is introduced into reactor 12. Reactor 12 is maintained at a specific temperature and to carry out the reaction air (oxygen-containing gas) is supplied thereto through air supply pipe 23. The portion of the reaction solution exceeding a predetermined fluid level is withdrawn using pipe 25.

Distillation column 13 is equipped with a heater (not shown) at the bottom and a condenser (not shown) at the top, thereby allowing a portion of a fraction condensed at the column top to reflux. The reaction solution supplied to distillation column 13 via pipe 25 is separated according to liquid/vapor equilibrium. Unreacted alcohol is obtained from the column top, water generated in the reaction is removed from sidecut pipe 28 provided in the middle, the desired α-hydroxycarboxylic acid ester is obtained from withdrawal pipe 29 in the middle, and by-products generated from the unreacted 1,2-diol, e.g., an α-hydroxycarboxylic acid, α-hydroxycarboxylic acid hydroxyalkyl ester, and α-hydroxycarboxylic acid ester oligomer, are obtained from the bottom.

The alcohol taken out from the column top recirculates as an unreacted starting material to reactor 11 via pipe 26. In a similar manner, the 1,2-diol withdrawn at the bottom flows back as an unreacted starting material to reactor 11 through pipe 27. In so doing, the α-hydroxycarboxylic acid, α-hydroxycarboxylic acid hydroxyalkyl ester, and α-hydroxycarboxylic acid ester oligomer flowing back together inhibit side reactions in reactors 11 and 12. When the alcohol and/or 1,2-diol of the unreacted starting materials flow back, the amount of the starting materials replenished through ingredients feed pipe 21 corresponds to that used in the reaction and lost in the purification.

As the supply of the unreacted starting materials continues and by-products accumulate in the system, a portion of the column top fraction or the column bottom solution containing these by-products can be removed via purge tubes 30 and 31 by taking advantage of their boiling points.

Moreover, the water content of the unreacted starting materials supplied back can be lessened by partially or entirely removing water from sidecut pipe 28, thereby inhibiting a reduction in the α-hydroxycarboxylic acid ester yield of the reaction.

2. α-Hydroxycarboxylic Acid Condensates.

The α-hydroxycarboxylic acid condensates of the invention are categorized into the following 3 types (I) to (III):

(I)

an α-hydroxycarboxylic acid condensate having an α-hydroxycarboxylic acid condensate portion represented by General Formula 2:

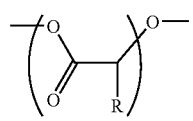

(2)

wherein R is hydrogen or $C_{1-5}$ alkyl, and the alkyl may be substituted and a 1,2-diol chain represented by General Formula 3:

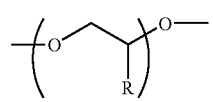

(3)

wherein R is hydrogen or $C_{1-5}$ alkyl, and the alkyl may be substituted, both terminals being represented by General Formula 4:

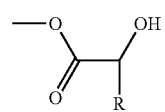

(4)

wherein R is hydrogen or $C_{1-5}$ alkyl, and the alkyl may be substituted, or General Formula 5:

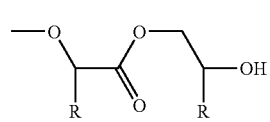

(5)

wherein each R is hydrogen or $C_{1-5}$ alkyl, and the alkyl may be substituted;

(II)

an α-hydroxycarboxylic acid condensate represented by General Formula 6:

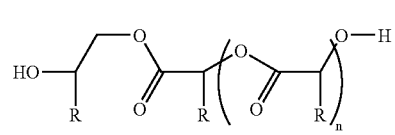

(6)

wherein each R is hydrogen or $C_{1-5}$ alkyl, the alkyl may be substituted, and n is within the range of 1 to 200; and (III)

an α-hydroxycarboxylic acid condensate represented by General Formula 7:

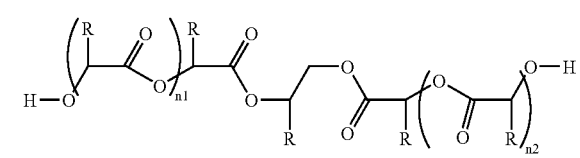

(7)

wherein each R is hydrogen or $C_{1-5}$ alkyl, the alkyl may be substituted, both n1 and n2 are 1 or more, and n1+n2 is within the range of 2 to 200.

In General Formula 2 showing the constitutional unit of an α-hydroxycarboxylic acid condensate of the invention, R is hydrogen or $C_{1-5}$ alkyl. Each R may be the same or different within the condensate molecule. The alkyl may be substituted. For example, when R is hydrogen, the α-hydroxycarboxylic acid condensate is a glycolic acid condensate. When R is a methyl group, it is a lactic acid condensate. Similarly, in General Formula 3, R is hydrogen or $C_{1-5}$ alkyl, and each R may be the same or different within the condensate molecule. The alkyl may be substituted. When R is hydrogen, General Formula 3 represents an ethylene glycol link. When R is a methyl group, it represents a propylene glycol link. The α-hydroxycarboxylic acid condensate of the invention contains the constitutional units represented by General Formulas 2 and 3, and both terminals of the condensate are represented by General Formula 4 or 5. Therefore, the condensate of the invention has a hydroxyl group at both terminals.

The α-hydroxycarboxylic acid condensate of the invention may have constitutional units other than those represented by General Formulas 2 and 3 and may be a copolymer with other components. Examples of copolymerization components include oxalic acid, malonic acid, succinic acid, glutaric acid, adipic acid, 1,4-cyclohexanedicarboxylic acid, diglycolic acid, and like dicarboxylic acids; and 1,4-cyclohexanedimethanol, diethylene glycol, triethylene glycol, and like diols.

The proportion of the constitutional unit represented by General Formula 2 in the α-hydroxycarboxylic acid condensate of the invention is preferably at least 70 wt. %, more preferably at least 80 wt. %, and most preferably 90 wt. % or more.

The α-hydroxycarboxylic acid condensate of the invention is highly crystalline and dense since it has an α-hydroxycarboxylic acid condensate portion and a 1,2-diol chain and contains in its main link many 2 carbon units.

More specific examples of the α-hydroxycarboxylic acid condensate are those that have a 1,2-diol ester at their terminal as represented by General Formula 6 (Condensate II). In General Formula 6, R is hydrogen or $C_{1-5}$ alkyl; each R may be the same or different; the alkyl may be substituted; and n is within the range of 1 to 200.

Specific examples also include condensates wherein α-hydroxycarboxylic acid condensates are bonded to both ends of a 1,2-diol as represented by General Formula 7 (Condensate III). In this formula, R is hydrogen or $C_{1-5}$ alkyl; each R may be the same or different within the condensate molecule; the alkyl may be substituted; both n1 and n2 is respectively 1 or more; and n1+n2 is within the range of 2 to 200.

Because these α-hydroxycarboxylic acid condensates have a hydroxyl group at both terminals, they can be readily macromolecularized through the use of chain extending agents. Common chain extending agents can be used to increase their molecular weight. Examples of chain extending agents include polyacid anhydrides, polycarboxylic acids, polyesters, polyisocianates, polyfunctional oxazoline compounds, polyfunctional aziridine compounds, carbonate compounds, epoxy compounds, silane coupling agents, phosphoric acid esters, phosphorous acid esters, alkyl zincs, alkyl aluminums, etc.

The α-hydroxycarboxylic acid condensates described above are industrially useful as raw materials for a variety of synthetic resins.

Production method for Condensates I to III (A. Outline of Production Method)

α-hydroxycarboxylic acid condensates I to III can be produced by condensing the α-hydroxycarboxylic acid hydroxyalkyl ester represented by General Formula 8 below by subjecting it to a 1,2-diol eliminating reaction:

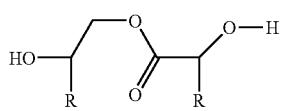

(8)

When R is hydrogen in General Formula 8, the compound represented by the formula is 2-hydroxyethyl glycolate, and the by-product 1,2-diol is ethylene glycol. When R is methyl, the compound represented by the formula is 2-hydroxypropyl lactate and the by-product 1,2-diol is 1,2-propanediol.

In the reaction, a plurality of α-hydroxycarboxylic acid hydroxyalkyl esters wherein each R in General Formula 8 may be different can be used.

The hydroxyl group of the hydroxycarboxylic acid portion of the α-hydroxycarboxylic acid ester represented by General Formula 8 is located at the α position. Therefore, side reactions such as intramolecular dehydration and the like do not occur during reaction and intermolecular condensation preferentially occurs, resulting in the production of condensate in high yield.

The reaction temperature should be 70 to 240° C., preferably 90 to 230° C., and more preferably 110 to 220° C. Excessively low reaction temperatures cause the reaction to proceed too slowly, resulting in low production efficiency. Excessively high reaction temperatures cause the reaction products to be heavy, colored, etc. An excessively high temperature at the initial stage of the reaction sometimes results in a decreased yield because the α-hydroxycarboxylic acid hydroxyalkyl ester evaporates. Therefore, the reaction temperature should be gradually increased.

Although use of a catalyst is not mandatory in the reaction, a catalyst can be used to increase the reaction rate. Examples of catalysts include hydrochloric acid, nitric acid, sulfuric acid, phosphoric acid, heteropolyacids, p-toluenesulfonic acid, methanesulfonic acid, glycolic acid, acidic ion-exchange resins, zeolites, clays, and like acidic catalysts; tin(II)chloride, tin(IV)chloride, dibutyltin oxide, tin(II)oxide, tin(IV) oxide, tin(II)octanoate, and like tin catalysts; titanium tetraisopropoxide, titanium tetrachloride, and like titanium catalysts; antimony trioxide, lead oxide, zinc oxide, aluminum oxide, like metal oxide catalysts; and the like. These catalysts can be used alone or in combination.

As the reaction is an equilibrium reaction, the reaction can be made to progress efficiently by shifting the equilibrium by removing from the system the 1,2-diol generated therein.

At the early stage of the reaction, the α-hydroxycarboxylic acid hydroxyalkyl ester is sometimes distilled off together with the generated 1,2-diol. In this case, by connecting a distillation column with a reactor to create reflux, the 1,2-diol and α-hydroxycarboxylic acid hydroxyalkyl ester can be isolated, and by withdrawing the purified 1,2-diol therefrom, the α-hydroxycarboxylic acid condensate can be produced in a high yield.

The 1,2-diol generated has a high boiling point. To efficiently remove it, the system should preferably be depressurized. The preferable pressure is 0.08 MPa or less, and more preferably 0.06 MPa or less. Moreover, by using an inactive gas such as nitrogen or helium, the 1,2-diol can be withdrawn via such a gas.

The 1,2-diol distilled off can be reused in a production process for an α-hydroxycarboxylic acid hydroxyalkyl ester as described below. The 1,2-diol fraction to be reused may contain an α-hydroxycarboxylic acid hydroxyalkyl ester that is concomitantly distilled off.

(B. Production Process of the Starting Material for Producing the Condensate)

The starting material, i.e., α-hydroxycarboxylic acid hydroxyalkyl ester, for producing the condensates can be preferably prepared, for example, by the reaction between the 1,2-diols as described above in connection with the process for producing the α-hydroxycarboxylic acid ester of the invention.

Types of 1,2-diols, reaction conditions, details of catalysts usable as necessary, and other conditions are as described above.

The α-hydroxycarboxylic acid hydroxyalkyl ester per se can be used in the production of the condensates, and it can also be used after purification. Purification is conducted according to known methods such as distillation, extraction, and the like.

The reaction solution contains water generated in the reaction, unreacted 1,2-diols, and the like that have boiling points lower than that of the ester produced from the reaction. Therefore, the column bottom solution left after removing these low-boiling-point components by distillation can be used in the condensation reaction. The unreacted 1,2-diols distilled off can also be reused in the reaction. Continuous distillation can be efficiently conducted by withdrawing water from the column top, the 1,2-diols from a sidecut part, and the α-hydroxycarboxylic acid hydroxyalkyl ester from the column bottom.

When the α-hydroxycarboxylic acid hydroxyalkyl ester produced is to be further purified, the α-hydroxycarboxylic acid hydroxyalkyl ester, after removing low-boiling-point components as described above, is further subjected to distillation and removed from the column top. In this instance, distillation is preferably conducted under reduced pressure. When an α-hydroxycarboxylic acid hydroxyalkyl ester is heated, it oligomerizes and releases a 1,2-diol. Therefore, there is the possibility that the α-hydroxycarboxylic acid hydroxyalkyl ester distilled off may be contaminated with the 1,2-diol, and the yield may be decreased in purifying the α-hydroxycarboxylic acid hydroxyalkyl ester. Conducting distillation under low pressure can keep the temperature in the distillation column low and therefore inhibit oligomerization. The pressure is preferably no more than 80000 Pa.

BRIEF DESCRIPTION OF THE DRAWINGS

(Description of Numerals)
11 and 12: Reactors
13: Distillation column
22 and 23: Air supply pipes
28 and 29: Sidecut pipes

BEST MODE FOR CARRYING OUT THE INVENTION

Figure 1:
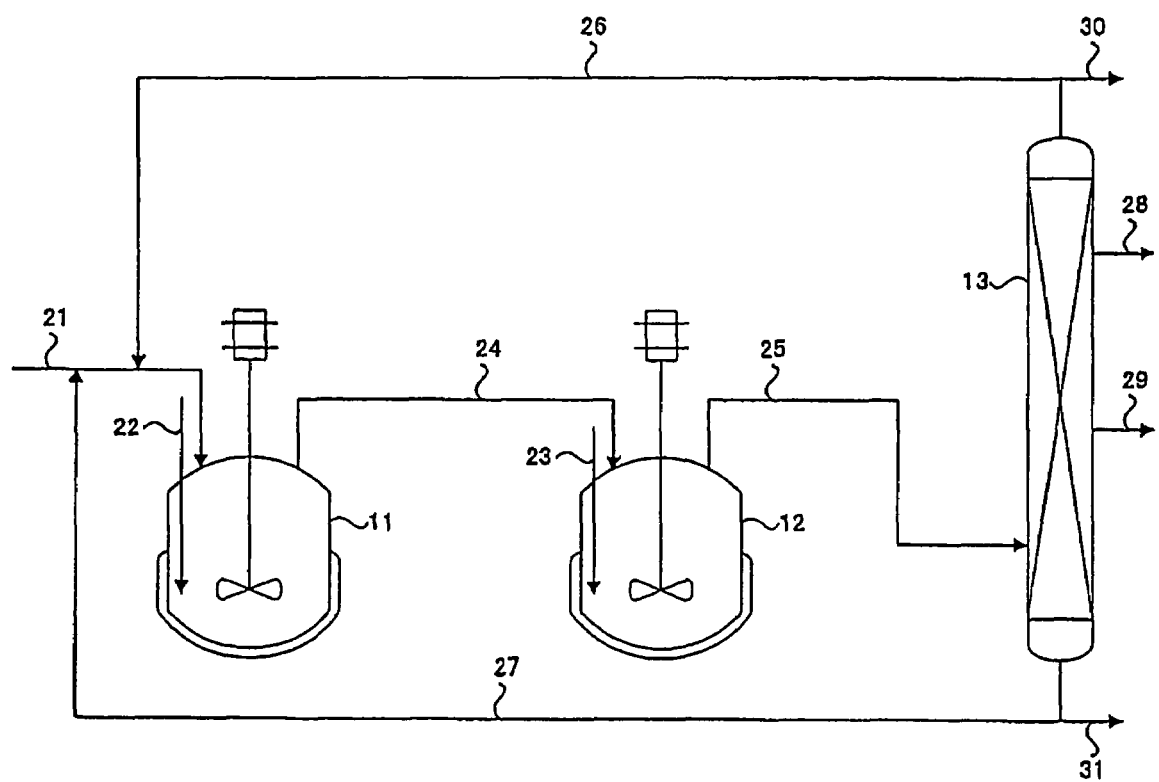
FIG. 1: A flow chart showing an example of a reaction setup equipped with continuous stirred tank reactors.

Examples and Comparative Examples are given below to illustrate the invention in more detail, but the scope of the invention is not limited to these examples.

Methods for measuring physical properties employed in Examples, Comparative Examples, and Reference Examples are as follows:

(1) Amount of metal fine particles supported

The amount of metal fine particles supported was measured by fluorescent X-ray analysis.

(2) Average particle diameter of metal fine particles

Particle diameters were measured by a transmission electron microscope (TEM) (trade name: HF-2000, manufactured by Hitachi seisakusyo, Ltd., acceleration voltage: 200 kV), and the particle composition was analyzed by the attached x-ray analyzer.

(3) Quantitative analysis of reaction products

The components of the reaction products found in the reaction solutions were quantitatively analyzed by gas chromatography and/or liquid chromatography.

REFERENCE EXAMPLE 1

Preparation of Au/TiO$_2$—SiO$_2$ Catalyst

TiO$_2$—SiO$_2$ prepared by coprecipitation (molar ratio: TiO$_2$/SiO$_2$=5/95, calcining temperature: 600° C., 50 to 250 mesh) was used as a carrier.

The pH of tetrachloroaurate (40 L, 20 mmol/L) was adjusted to pH 7 at a temperature of 65 to 75° C. using 0.5 N sodium hydroxide. To this aqueous solution, 1 kg of the TiO$_2$—SiO$_2$ carrier was added while being stirred. The solution was stirred for 1 hour while the temperature was maintained at 65 to 70° C. Subsequently, the solution was left to stand, the supernatant thereof was removed, the remaining immobilized gold was mixed with 20 L of ion-exchanged water and stirred for five minutes at room temperature, and the supernatant was again removed. This washing process was repeated 3 times. Ultimately, the immobilized gold obtained by filtration was dried for 8 hours at 110° C. and sintered for 3 hours in the air at 400° C., thereby producing a catalyst (Au/TiO$_2$—SiO$_2$) wherein gold is supported on a TiO$_2$—SiO$_2$ carrier.

The amount of gold supported by the carrier in this catalyst was 5.4 wt. %. When the diameter of the gold particles was measured, almost all particles were highly dispersed and had a diameter of no more than 6 nm and a narrow particle diameter distribution with a peak in the vicinity of 2 to 3 nm. The average particle diameter was no more than 6 nm.

EXAMPLE 1-1

Synthesis of Methyl Glycolate

An α-hydroxycarboxylic acid ester (methyl glycolate) was synthesized using the Au/TiO$_2$—SiO$_2$ catalyst prepared in Reference Example 1.

A 100-L reactor equipped with a rotary stirrer and condenser was charged with 9.6 kg of ethylene glycol, 50.0 kg of methanol, and 4.3 kg of the catalyst obtained in Reference Example 1. The pressure was increased to 0.7 MPa by nitrogen. Subsequently, the pressure was adjusted to 1 MPa by increasing the inner temperature to 120° C. While the pressure was maintained at 1 MPa, reaction was carried out for 8 hours at a temperature of 120° C. by blowing air at a rate of 2.5 Nm$^3$/hr into the solution.

After the reaction, the reaction solution was cooled and taken out. After filtering the catalyst, the reaction solution was analyzed by gas and liquid chromatography and a Karl Fischer moisture meter. The reaction solution contained 7.5 kg of methyl glycolate, 3.5 kg of ethylene glycol, 43.2 kg of methanol, 4.9 kg of water, and 0.7 kg of glycolic acid. Therefore, conversion of ethylene glycol was 63.5 mol %, and the yield for methyl glycolate was 53.8 mol % calculated based on ethylene glycol.

The reaction solution obtained above was charged into a rotary thin-film evaporator to remove low-boiling-point components. Low-boiling-point components were removed under the conditions of a jacket temperature of 140° C. and a pressure of 533 hPa. The composition of the reaction solution thus obtained from which the low-boiling-point fraction had been removed consisted of 47.0 wt. % of methyl glycolate, 26.0 wt. % of methanol, 17.0 wt. % of water, 7.0 wt. % of ethylene glycol, and 2.6 wt. % of glycolic acid.

The aforementioned reaction solution (3050 g) was charged into a 3-L glass flask equipped with a distillation column packed with Sulzer Labo packings to a height of 90 cm to conduct batch distillation. Initially, the low-boiling-point components, i.e., methanol and water, were removed at a reflux ratio of 0.5 under a column top pressure of 133 hPa. A fraction containing methyl glycolate was then removed at a reflux ratio of 1 under a column top pressure of 13 hPa. The temperature at the top of the column at this time was 46 to 47° C. Analysis revealed that the methyl glycolate-containing fraction contained 98.9 wt. % of methyl glycolate, 0.10 wt. % of methanol, and 0.31 wt. % of water.

EXAMPLE 1-2

The low-boiling-point components obtained by the rotary thin-film evaporator in Example 1-1 and the initial distillate of methyl glycolate were combined and introduced to the bottom of a 15-stage Oldershaw distillation column and subjected to batch distillation. The distillation column was operated at a reflux ratio of 1 and a fraction containing methanol in a proportion of 97 wt. % and water in a proportion of 3 wt. % was obtained from the column top.

A 500-mL reactor equipped with a rotary stirrer and condenser was charged with 24.1 g of ethylene glycol, 127.8 g of the fraction obtained from the distillation described above, and 18.0 g of the catalyst prepared in Reference Example 1. These ingredients contained water in a proportion of 2.5 wt. %. The pressure was increased to 0.7 MPa by nitrogen. Subsequently, the pressure was adjusted to 1 MPa by increasing the inner temperature to 120° C. While the pressure was maintained at 1 MPa, reaction was carried out for 4 hours at a temperature of 120° C. by blowing a mixed gas containing oxygen in a proportion of 8 volume % and nitrogen in a proportion of 92 volume % at a rate of 1 normal liter per minute into the solution.

After the reaction, the reaction solution was cooled and removed. After filtering the catalyst, the reaction solution was analyzed by gas and liquid chromatography. The reaction solution contained 19.9 g of methyl glycolate, 3.9 g of ethylene glycol, and 114.2 g of methanol. Therefore, conversion of ethylene glycol was 83.7 mol %, and yield of methyl glycolate was 56.9 mol % based on ethylene glycol.

COMPARATIVE EXAMPLE 1

A 500-mL autoclave equipped with a rotary stirrer and condenser was charged with 24.1 g of ethylene glycol, 198 g of the initial distillate obtained in the distillation of methyl glycolate in Example 1-1 (water content: 37 wt. %), and 18.0 g of the catalyst prepared in Reference Example 1. These ingredients had a water content of 33 wt. %. The pressure was increased to 0.7 MPa by nitrogen. Subsequently, the pressure was adjusted to 1 MPa by increasing the inner temperature to 120° C. While the pressure was maintained at 1 MPa, reaction was carried out for 4 hours at a temperature of 120° C. by blowing a mixed gas containing oxygen in a proportion of 8 volume % and nitrogen in a proportion of 92 volume % at a rate of 1 normal liter per minute into the solution.

After the reaction, the reaction solution was cooled and taken out. After filtering the catalyst, the reaction solution was analyzed by gas and liquid chromatography. The reaction solution contained 13.8 g of methyl glycolate, 4.3 g of ethylene glycol, and 115.3 g of methanol. Therefore, conversion of ethylene glycol was 82.2 mol %, and yield of methyl glycolate was 39.4 mol % based on ethylene glycol.

EXAMPLE 2-1

The reaction solution obtained in Example 1-1 was purified.

A distillation column packed with Dickson packings thereby having 5 theoretical stages equipped with a rotary thin-film evaporator at the bottom was used as a distillation setup. The reaction solution obtained in Example 1-1 was continuously supplied to this distillation setup. The distillation setup was operated at a column top pressure of 66.7 kPa and a reflux ratio of 1, and a fraction containing methanol and water was withdrawn from the column top as a column top solution. In contrast, the column bottom solution was supplied back to the same distillation setup and subjected to the second distillation. The column top solution (the second column top solution) and the column bottom solution (the second column bottom solution) were then taken out. The pressure at the top of the column at the time was 13.3 kPa and the reflux ratio was 1.

The second column top solution and the second column bottom solution were analyzed by gas and liquid chromatography. The purity of methyl glycolate in the second column top solution was 98 wt. %. Of the methyl glycolate supplied for the first distillation, the second column top solution contained it in a proportion of 83%, and the second column bottom solution contained it in a proportion of 16%, resulting in a loss of 2%. Compared with the by-product content of the reaction solution initially supplied, the increase of the by-product content in the second column bottom solution was 1 mol % for 2-hydroxyethyl glycolate and 1 mol % for methyl glycolate dimer relative to the methyl glycolate supplied.

EXAMPLE 2-2

The reaction solution produced in Example 1-1 was purified.

A distillation column packed with Dickson packings thereby having 5 theoretical stages equipped with a flask and a heating mantle at the bottom was used as a distillation setup. The reaction solution obtained in Example 1-1 was continuously supplied to this distillation setup. The distillation setup was operated at a column top pressure of 66.7 kPa and a reflux ratio of 1, and a fraction containing methanol and water was withdrawn from the column top as a column top solution. In contrast, the column bottom solution was supplied back to the same distillation setup and subjected to the second distillation. The column top solution (the second column top solution) and the column bottom solution (the second column bottom solution) were then taken out. The pressure at the top of the column at the time was 13.3 kPa and the reflux ratio was 1.

The second column top solution and the second column bottom solution were analyzed by gas and liquid chromatography. The purity of methyl glycolate in the second column top solution was 93 wt. %. Of the methyl glycolate initially supplied for the distillation, the second column top solution contained it in a proportion of 53%, and the second column bottom solution contained it in a proportion of 22%, resulting in a loss of 25%. Compared with the by-product content of the reaction solution initially supplied, the increase of by-product content in the second column bottom solution was 3 mol % for glycolic acid, 5 mol % for 2-hydroxyethyl glycolate, 2 mol % for ethylene glycol diglycolate, and 1 mol % for methyl glycolate dimer, relative to the methyl glycolate supplied.

The second column bottom solution had acquired very high viscosity, presumably because of the production of high-molecular-weight oligomers not detected by the chromatographical analysis.

EXAMPLE 3-1

Methyl glycolate was synthesized using the $Au/TiO_2$—$SiO_2$ catalyst prepared in Reference Example 1. A 500-mL autoclave equipped with a rotary stirrer and condenser was charged with 24.1 g of ethylene glycol, 124.1 g of methanol, 1.1 g of glycolic acid, and 18.0 g of the catalyst obtained in the Reference Example. The pressure was increased to 0.7 MPa by nitrogen. Subsequently, the pressure was adjusted to 1 MPa by increasing the inner temperature to 120° C. While the pressure was maintained at 1 MPa, reaction was carried out for 4 hours at a temperature of 120° C. by blowing a mixed gas containing oxygen in a proportion of 8 volume % and nitrogen in a proportion of 92 volume % at a rate of 1 normal liter per minute into the solution.

After the reaction, the reaction solution was cooled and removed. After filtering the catalyst, the reaction solution was analyzed by gas and liquid chromatography. The reaction solution contained 23.5 g of methyl glycolate, 1.2 g of 2-hydroxyethyl glycolate, 2.0 g of ethylene glycol, and 1.2 g of glycolic acid. Therefore, conversion of ethylene glycol was 92 mol %, and yield of methyl glycolate was 67 mol % based on ethylene glycol.

EXAMPLE 3-2

A reaction was conducted in the same manner as in Example 3-1 except that the reaction ingredients did not contain glycolic acid. After the reaction, the reaction solution was cooled and removed. After filtering the catalyst, the reaction solution was analyzed by gas and liquid chromatography. The reaction solution contained 22.2 g of methyl glycolate, 1.4 g of 2-hydroxyethyl glycolate, 1.8 g of ethylene glycol, and 0.9 g of glycolic acid. Therefore, conversion of ethylene glycol was 92 mol %, and yield of methyl glycolate was 63 mol % based on ethylene glycol.

EXAMPLE 4-1

The analysis of the solution obtained at the bottom of the distillation column after purifying methyl glycolate in Example 1-1 revealed that the solution contained 0.3 wt. % of methanol, 0.2 wt. % of water, 5.8 wt. % of methyl glycolate, 2.0 wt. % of ethylene glycol, 1.6 wt. % of glycolic acid, and 14.8 wt. % of 2-hydroxyethyl glycolate. The column bottom solution was viscous and contained, other than the above components, a methyl glycolate oligomer, and 2-hydroxyethyl glycolate oligomer.

A 500-mL autoclave equipped with a rotary stirrer and condenser was charged with 24.1 g of ethylene glycol, 124.1 g of methanol, 18.0 g of the catalyst prepared in the Reference Example 1, and 10 g of the solution obtained at the bottom of the distillation column in Example 1-1 (containing 0.58 g of methyl glycolate, 1.48 g of 2-hydroxyethyl glycolate, 0.2 g of ethylene glycol, and 0.16 g of glycolic acid). The pressure was increased to 0.7 MPa by nitrogen. Subsequently, the pressure was adjusted to 1 MPa by increasing the inner temperature to 120° C. While the pressure was maintained at 1 MPa, reaction was carried out for 4 hours at a temperature of 120° C. by blowing a mixed gas containing oxygen in a proportion of 8 volume % and nitrogen in a proportion of 92 volume % at a rate of 1 normal liter per minute into the solution.

After the reaction, the reaction solution was cooled and removed. After filtering the catalyst, the reaction solution was analyzed by gas and liquid chromatography. The reaction solution contained 27.1 g of methyl glycolate, 2.3 g of 2-hydroxyethyl glycolate, 2.3 g of ethylene glycol, and 0.9 g of glycolic acid.

EXAMPLE 4-2

A reaction was conducted in the same manner as in Example 4-1 except that the reaction ingredients introduced to the autoclave did not include the distillation column bottom solution.

After the reaction, the reaction solution was cooled and taken out. After filtering the catalyst, the reaction solution was analyzed by gas and liquid chromatography. The reaction solution contained 22.2 g of methyl glycolate, 1.4 g of 2-hydroxyethyl glycolate, 1.8 g of ethylene glycol, and 0.9 g of glycolic acid.

EXAMPLE 4-3

An autoclave was charged with 10.0 g of the solution obtained at the bottom of the distillation column in Example 1-1, 100.5 g of methanol, and 0.5 g of a strongly acidic cation-exchange resin (trade name: Dowex 50 W-X8, manufactured by Dow Chemical Company). These ingredients were heated while being stirred for 3 hours at a temperature of 100° C. After cooling the reaction solution, the cation-exchange resin was removed by filtration, and the reaction solution thus obtained was analyzed by gas and liquid chromatography. The reaction solution contained 6.0 g of methyl glycolate, 1.2 g of 2-hydroxyethyl glycolate, 0.35 g of ethylene glycol, and 0.02 g of glycolic acid.

Reaction was conducted in the same manner as in Example 4-1 by adding to the aforementioned reaction solution 23.5 g of ethylene glycol, 28.2 g of methanol, and 18.0 g of the catalyst prepared in Reference Example 1. After the reaction, the reaction solution was cooled and removed. After filtering the catalyst, the reaction solution was analyzed by gas and liquid chromatography and a Karl Fischer moisture meter. The reaction solution contained 28.5 g of methyl glycolate, 2.5 g of 2-hydroxyethyl glycolate, 2.2 g of ethylene glycol, and 1.0 g of glycolic acid.

EXAMPLE 5-1

The reaction solution obtained in Example 1-1 was purified.

In conjunction with the continuous supply of the reaction solution obtained in Example 1-1 to a 50-stage distillation column at the $20^{th}$ stage counted from the top, a fraction containing methanol and water was withdrawn from the top of the column (solution A), a fraction containing methyl glycolate was removed from the $10^{th}$ stage from the top (solution B), and a fraction containing ethylene glycol was obtained from the bottom of the column (solution C). The pressure at the top of the column was set at 13.3 kPa and the reflux ratio at 1.

Solutions A, B and C were analyzed by gas and liquid chromatography. The purity of methyl glycolate in solution B was 99 wt. %. Of the methyl glycolate supplied, solution B contained it in a proportion of 83%, and solution C contained it in a proportion of 10%, resulting in a loss of 6%. Compared with the by-product content of the reaction solution supplied, the increase of the by-product content in solution C was 1 mol % for glycolic acid, 3 mol % for 2-hydroxyethyl glycolate, and 2 mol % for methyl glycolate dimer, relative to the methyl glycolate.

EXAMPLE 5-2

The reaction solution obtained in Example 1-1 was purified using two distillation columns (each having 15 stages).

After continuously supplying the reaction solution to a 15-stage distillation column (first distillation column) at the $10^{th}$ stage counted from the top, a fraction containing methanol and water was withdrawn from the top of the column (solution D). The pressure at the top of the column was set at 66.7 kPa and the reflux ratio at 1.

Successively, the solution obtained at the bottom of the first distillation column was continuously supplied to the second distillation column at the $10^{th}$ stage counted from the column top. Subsequently, a fraction containing methyl glycolate was taken out from the second column top (solution E). The pressure at the top of the second column was set at 13.3 kPa and the reflux ratio at 1.

Solutions D and E were analyzed by gas and liquid chromatography. The purity of methyl glycolate in solution E was 92 wt. %. Of the methyl glycolate supplied, solution E contained it in a proportion of 59%, and the solution at the bottom of the second column contained it in a proportion of 9%, resulting in a loss of 32%. Compared with the by-product content of the reaction solution initially supplied, the increase of by-product content in the bottom solution of the second column was 3 mol % for glycolic acid, 5 mol % for 2-hydroxyethyl glycolate, and 8 mol % for methyl glycolate dimer, relative to the methyl glycolate supplied. The bottom solution of the second distillation column had acquired very high viscosity, presumably because of the presence of high-molecular-weight oligomers not detected by the chromatographical analysis.

EXAMPLE 6

A continuous reaction was carried out as shown in FIG. 1. The reaction setup consisted of two 500-L stirred tank reactors connected together and a distillation column with an inner diameter of 250 mm having 30 stages in total. To each reactor, 16 kg of the catalyst prepared in Reference Example 1 was introduced and used in a suspended bed. The reaction temperature was 120° C., and the residence time in each reactor was 7 hours. The amount of ingredients supplied, including unreacted ingredients supplied back, when the reaction came to steady state was 27 kg/hr for methanol, 10 kg/hr for ethylene glycol, 0.5 kg/hr for water, 2.4 kg/hr for 2-hydroxyethyl glycolate, and 4.4 kg/hr for methyl glycolate oligomer. The ingredients contained water in a proportion of 0.7 wt. %.

The reaction products taken out from the second reactor included 19 wt. % of methyl glycolate. The reaction products were distilled by introducing them into the distillation column at the $20^{th}$ stage counted from the top.

The amount of methyl glycolate withdrawn from a sidecut part provided at the $15^{th}$ stage counted from the column top was 8.3 kg/hr. The amount of water withdrawn from a sidecut part provided at the $10^{th}$ stage was 5.2 kg/hr.

The methanol obtained at the top of the column was supplied to the first reactor. The solution obtained at the bottom was also supplied to the first reactor while a portion of this solution was purged. The proportion of water removed from the reaction products by distillation was 98%. The water content of the fraction containing the supplied methanol and ethylene glycol was 1.5 wt. %.

Methods for measuring physical properties employed in Examples 7-1 and 7-2 are as follows:

(1) Melting Point

Using a differential scanning calorimeter (DSC 2000) manufactured by Seiko Instruments Inc., test samples (10 mg) were introduced into an aluminum pan and heated from 20° C. to 300° C. at a rate of 10° C./min. The melting point refers to the endothermic peak maximum.

(2) Weight-Average Molecular Weight

A gel permeation chromatography (GPC) manufactured by Tosoh Corporation was used. Hexafluoroisopropanol was used as an eluant, and a single HFIP-LG and a pair of HFIP-806 manufactured by Shodex were used as columns. Calibration curves were prepared based on polymethyl methacrylate standards of known molecular weight.

EXAMPLE 7-1

2-Hydroxyethyl glycolate was synthesized using the $Au/TiO_2$—$SiO_2$ catalyst prepared in Reference Example 1. A 500-mL autoclave equipped with a rotary stirrer and condenser was charged with 246.3 g of ethylene glycol and 8.14 g of the catalyst of the Reference Example 1. The pressure was increased to 0.7 MPa by nitrogen. Subsequently, the pressure was adjusted to 2 MPa by increasing the inner temperature to 110° C. While the pressure was maintained at 2 MPa, reaction was carried out for 9 hours at a temperature of 110° C. by blowing the air into the solution. The rate of air supply was adjusted such that the gas exhausted at the outlet port of the condenser had an oxygen concentration of 5 volume % at most.

After the reaction, the reaction solution was cooled and removed. After filtering the catalyst, the reaction solution was analyzed by gas and liquid chromatography. The reaction solution contained 66.0 g of 2-hydroxyethyl glycolate, 7.5 g of glycolic acid, and 166.1 g of ethylene glycol. Therefore, conversion of ethylene glycol was 32.5 mol %, and the yield of 2-hydroxyethyl glycolate was 27.7 mol % based on ethylene glycol.

This reaction solution was then subjected to batch distillation under reduced pressure using a 20-stage glass Oldershaw distillation column. The reaction solution was charged into the column at the bottom. The low-boiling-point components, i.e., water and ethylene glycol, were distilled off from the top of the column, and the solution containing concentrated 2-hydroxyethyl glycolate was obtained at the bottom. This column bottom solution contained 2-hydroxyethyl glycolate in a proportion of 91.5 wt. %, glycolic acid in a proportion of 3.2 wt. %, and ethylene glycol in a proportion of 4.2 wt. %.

A condensate was produced by charging 150 g of the column bottom solution into a 300-mL separable flask equipped with a stirrer and condenser and adding thereto 0.11 g of tin(IV) chloride pentahydrate as a catalyst. The flask was heated to 200° C. in an oil bath, and the ethylene glycol generated was distilled off. As the reaction progressed, the pressure was gradually decreased while nitrogen was introduced into the flask to enhance the distillation of ethylene glycol. The reaction was stopped 15 hours after the beginning of the reaction. After cooling, brown solid matter was obtained.

This solid matter had a melting point of 182° C. and a weight-average molecular weight of 10800.

EXAMPLE 7-2

Distillation was conducted in the same manner as in Example 7-1. After distilling off the low-boiling-point components (water and ethylene glycol) from the top of the column, distillation was continued, and a fraction containing 2-hydroxyethyl glycolate was withdrawn from the column top. This fraction was obtained under a column top pressure of 347 Pa at a column top temperature of 133 to 134° C. Gas chromatography and Karl Fischer moisture meter analysis revealed that the fraction contained 2-hydroxyethyl glycolate in a proportion of 95.1 wt. %, ethylene glycol in a proportion of 4.4 wt. %, and water in a proportion of 0.4 wt. %.

By charging 150 g of the aforementioned fraction into a 300-mL separable flask equipped with a stirrer and condenser and adding thereto 78 mg of dibutyltin oxide as a catalyst, a condensate was produced. The flask was heated to 180° C. in an oil bath, and the ethylene glycol generated was distilled off. As the reaction progressed, the pressure was gradually decreased. The reaction was stopped 13 hours after the beginning of the reaction. The pressure at the end of the reaction was 667 Pa. After cooling, light brown solid matter was obtained. Analysis of the solid matter revealed a melting point of 178° C. and a weight-average molecular weight of 6700.

Figure 2:
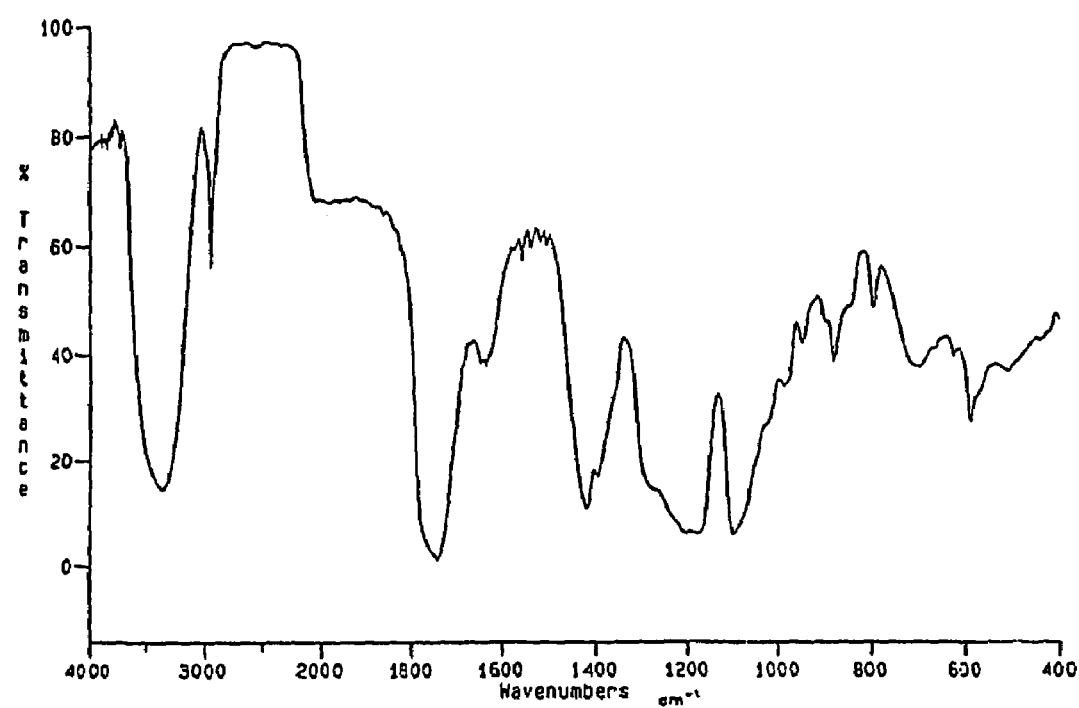
FIG. 2: An FT-IR spectrum of the α-hydroxycarboxylic acid condensate obtained in Example 7-2.

The FT-IR spectrum shown in FIG. 2 exhibits the following absorption peaks: alcoholic hydroxyl group C—O stretching vibrations near 1100 $cm^{-1}$, ester group C—O stretching vibrations near 1200 $cm^{-1}$, O—H bending vibrations near 1420 $cm^{-1}$, ester C=O stretching vibrations near 1740 $cm^{-1}$, and O—H stretching vibrations near 3300 $cm^{-1}$.

Figure 3:
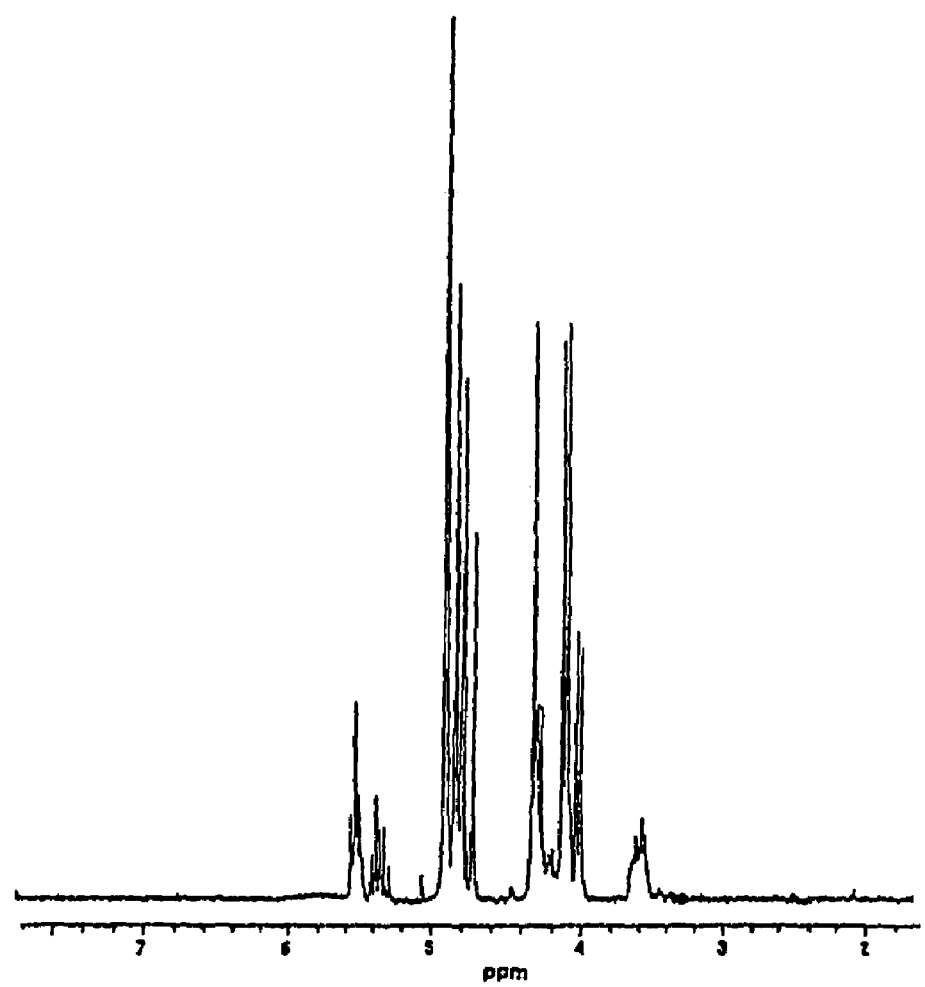
FIG. 3: A $^1$H-NMR spectrum of the α-hydroxycarboxylic acid condensate obtained in Example 7-2.

The $^1$H-NMR spectrum shown in FIG. 3 reveals the following chemical shifts: methylene groups bonded to terminal hydroxyl groups between 4 and 4.4 ppm, methylene groups of condensed glycolic acid regions between 4.7 and 4.9 ppm, and terminal hydroxyl group between 5.2 and 5.6 ppm.

INDUSTRIAL APPLICABILITY

The process for producing an α-hydroxycarboxylic acid ester disclosed herein, compared with the prior art production processes, inhibits or prevents side reactions, and therefore can more efficiently produce the desired α-hydroxycarboxylic acid ester.

The α-hydroxycarboxylic acid ester thus obtained is usable, for example, as a raw material for various synthetic resins such as polyglycolic acid and the like. Also, the α-hydroxycarboxylic acid ester can preferably be used as a cleaning agent for boilers and the like as well as an etchant, etc.

The α-hydroxycarboxylic acid condensate of the present invention is industrially beneficial as a raw material for various synthetic resins.

The invention claimed is:

1. A process for producing an α-hydroxycarboxylic acid ester comprising Steps 1 to 3:
   Step 1. reacting, in the presence of oxygen, (i) a 1,2-diol with a 1,2-diol or (ii) a 1,2-diol with an alcohol to obtain a reaction product containing an α-hydroxycarboxylic acid ester;
   Step 2. separating the α-hydroxycarboxylic acid ester from the reaction product obtained in Step 1 by distillation under reduced pressure; and
   Step 3. feeding Step 1 with a mixture obtained by partially or entirely removing water from the reaction product, wherein the mixture contains an unreacted 1,2-diol and/or alcohol.

2. A process according to claim 1, wherein the distillation of Step 2 is conducted at a pressure of 13 to 80000 Pa and a temperature at the bottom of a distillation column of 30 to 250° C.

3. A process according to claim 1, wherein the mixture in Step 3 contains water in a proportion of 0 to 20 wt. %.

4. A process according to claim 1, wherein when Steps 1 to 3 are in steady state, the reaction ingredients in Step 1 contain water in a proportion of 0.1 to 15 wt. %.

5. A process according to claim 1, wherein in Step 3 at least 30 wt. % of water based on the total weight of water is removed and fed to Step 1.

6. A process according to claim 1, wherein in the distillation of Step 2 the reaction product obtained in Step 1 is formed into a thin film and heated by contacting the thin film with a heating surface.

7. A process according to claim 1, wherein the reaction of Step 1 is conducted in the presence of a catalyst comprising a carrier and fine particles of a noble metal supported on the carrier.

8. A process according to claim 1, wherein the reaction of Step 1 is conducted by further adding an α-hydroxycarboxylic acid and/or α-hydroxycarboxylic acid ester oligomer.

9. A process according to claim 1, wherein a solution obtained at the bottom of a distillation column containing at least one reaction by-product selected from the group consisting of α-hydroxycarboxylic acids and α-hydroxycarboxylic acid ester oligomers generated in Step 1 and/or Step 2 is fed to Step 1 and/or Step 2.

10. A process according to claim 1, wherein a 1,2-diol and an alcohol are reacted in Step 1.

11. A process according to claim 10, wherein the reaction of Step 1 is conducted by further adding at least one member selected from the group consisting of α-hydroxycarboxylic acids, α-hydroxycarboxylic acid 2-hydroxyalkyl esters, and α-hydroxycarboxylic acid ester oligomers.

12. A process according to claim 10, wherein the reaction of Step 1 is conducted in the presence of a catalyst comprising a carrier and fine particles of a noble metal supported on the carrier.

13. A process according to claim 10, wherein in Step 2 a fraction containing the α-hydroxycarboxylic acid ester is collected from a sidecut part.

14. A process according to claim 10, wherein a solution obtained at the bottom of a distillation column containing at least one reaction by-product selected from the group consisting of α-hydroxycarboxylic acids, α-hydroxycarboxylic acid 2-hydroxyalkyl esters and α-hydroxycarboxylic acid ester oligomers generated in Step 1 and/or Step 2 is provided in Step 1 and/or Step 2.

15. A process according to claim 10, wherein a solution obtained at the bottom of a distillation column containing an α-hydroxycarboxylic acid ester oligomer generated in Step 1 and/or Step 2 is contacted with an alcohol R—OH corresponding to the ester group —C(=O)OR of the oligomer, whrein R is an organic residue, and then reused in Step 1 and/or Step 2.

16. A process according to claim 10, wherein the 1,2-diol is ethylene glycol and the α-hydroxycarboxylic acid ester is a glycolic acid ester.

* * * * *